United States Patent
Klein et al.

(10) Patent No.: US 9,149,478 B2
(45) Date of Patent: Oct. 6, 2015

(54) DIABETES THERAPY

(75) Inventors: Thomas Klein, Radolfzell (DE); Michael Mark, Biberach an der Riss (DE); Leo Thomas, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 563 days.

(21) Appl. No.: 13/166,892

(22) Filed: Jun. 23, 2011

(65) Prior Publication Data

US 2012/0165251 A1  Jun. 28, 2012

(30) Foreign Application Priority Data

Jun. 24, 2010  (EP) .................................. 10167243

(51) Int. Cl.
| | | |
|---|---|---|
| A61K 38/28 | (2006.01) | |
| A61K 31/522 | (2006.01) | |
| A61K 31/155 | (2006.01) | |
| A61K 45/06 | (2006.01) | |

(52) U.S. Cl.
CPC ............. *A61K 31/522* (2013.01); *A61K 31/155* (2013.01); *A61K 38/28* (2013.01); *A61K 45/06* (2013.01)

(58) Field of Classification Search
None
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |
| 5,051,517 A | 9/1991 | Findeisen et al. |
| 5,084,460 A | 1/1992 | Munson, Jr. et al. |
| 5,130,244 A | 7/1992 | Nishimaki et al. |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,248,758 B1 | 6/2001 | Klokkers et al. |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

Clinical Trial Identifier NCT00954447, "Efficacy and Safety of Linagliptin in Combination with Insulin in Patients with Type 2 Diabetes" update of Jun. 14, 2010, http://clinicaltrials.gov/archive/NCT00954447/2010_06_14, accessed Jul. 18, 2013.*

Kim et al., "KR-64236, 6-{2-[2-(5-cyano-4,5-dihydropyrazol-1yl)-2-oxoexthylamino]etylamino}nictinontrile, is a novel dipeptidyl peptidase IV (DPP-IV) inhibitor with anti-hyperglycemic activity," Eur. J. Pharm. 518:63-70 (2005).*

Holman, et al., "Addition of biphasic, prandial, or basal insulin to oral therapy in type 2 diabetes," N. Eng. J. Med. 357:1716-1730 (2007).*

(Continued)

*Primary Examiner* — Julie Ha
*Assistant Examiner* — Kristina M Hellman
(74) *Attorney, Agent, or Firm* — Michael P. Morris; Timothy X. Witkowski

(57) ABSTRACT

The present invention relates to methods for treating and/or preventing metabolic diseases comprising the combined administration of a DPP-4 inhibitor and a long-acting insulin. The invention further relates to a DPP-4 inhibitor for subcutaneous or transdermal use.

8 Claims, 1 Drawing Sheet

(56) References Cited

U.S. PATENT DOCUMENTS

| | | |
|---|---|---|
| 6,303,661 B1 | 10/2001 | Demuth et al. |
| 6,342,601 B1 | 1/2002 | Bantick et al. |
| 6,372,940 B1 | 4/2002 | Cavazza |
| 6,548,481 B1 | 4/2003 | Demuth et al. |
| 6,579,868 B1 | 6/2003 | Asano et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,995,183 B2 | 2/2006 | Hamann et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,235,538 B2 | 6/2007 | Kanstrup et al. |
| 7,247,478 B2 | 7/2007 | Eberhardt et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,407,995 B2 | 8/2008 | Ok et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,673,927 B2 | 3/2014 | Dugi et al. |
| 8,679,520 B2 | 3/2014 | Horres et al. |
| 8,785,455 B2 | 7/2014 | Hotter et al. |
| 8,865,729 B2 | 10/2014 | Sieger et al. |
| 8,962,636 B2 | 2/2015 | Pfrengle et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0078269 A1 | 4/2003 | Pearson et al. |
| 2003/0100563 A1 | 5/2003 | Edmondson et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0034922 A1 | 2/2006 | Cheng et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0060530 A1* | 3/2007 | Christopher et al. ........... 514/19 |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |

(56) References Cited

U.S. PATENT DOCUMENTS

| | | | |
|---|---|---|---|
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2011/0009391 A1 | 1/2011 | Braun et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0122089 A1 | 5/2013 | Kohlrausch et al. |
| 2013/0172244 A1 | 7/2013 | Klein et al. |
| 2013/0184204 A1 | 7/2013 | PFRENGLE et al. |
| 2013/0196898 A1 | 8/2013 | Dugi et al. |
| 2013/0236543 A1 | 9/2013 | Ito et al. |

FOREIGN PATENT DOCUMENTS

| | | |
|---|---|---|
| CA | 1123437 A1 | 5/1982 |
| CA | 2136288 A1 | 5/1995 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651019 A1 | 11/2007 |
| CA | 2651089 A1 | 11/2007 |
| CN | 101234105 A | 8/2008 |
| DE | 2205815 A1 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2006045156 A | 2/2006 |
| JP | 2010053576 A | 3/2010 |
| JP | 2010070576 A | 4/2010 |
| JP | 2010524580 A | 7/2010 |

(56) References Cited

FOREIGN PATENT DOCUMENTS

| | | | |
|---|---|---|---|
| KR | 20070111099 A | 11/2007 |
| WO | 9107945 A1 | 6/1991 |
| WO | 9205175 A1 | 4/1992 |
| WO | 9219227 A2 | 11/1992 |
| WO | 9402150 A1 | 2/1994 |
| WO | 9403456 A1 | 2/1994 |
| WO | 9532178 A1 | 11/1995 |
| WO | 9609045 A1 | 3/1996 |
| WO | 9611917 A1 | 4/1996 |
| WO | 9636638 A1 | 11/1996 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 | 3/1998 |
| WO | 9818770 A1 | 5/1998 |
| WO | 9822464 A1 | 5/1998 |
| WO | 9828007 A1 | 7/1998 |
| WO | 9840069 A2 | 9/1998 |
| WO | 9846082 A1 | 10/1998 |
| WO | 9856406 A1 | 12/1998 |
| WO | 9929695 A1 | 6/1999 |
| WO | 9938501 A2 | 8/1999 |
| WO | 9950248 A1 | 10/1999 |
| WO | 9956561 A1 | 11/1999 |
| WO | 9967279 A1 | 12/1999 |
| WO | 0073307 A2 | 12/2000 |
| WO | 0107441 A1 | 2/2001 |
| WO | 0140180 A2 | 6/2001 |
| WO | 0151919 | 7/2001 |
| WO | 0152825 | 7/2001 |
| WO | 0152825 A2 | 7/2001 |
| WO | 0152852 A1 | 7/2001 |
| WO | 0166548 A1 | 9/2001 |
| WO | 0168646 A1 | 9/2001 |
| WO | 0172290 A2 | 10/2001 |
| WO | 0177110 A1 | 10/2001 |
| WO | 0196301 A1 | 12/2001 |
| WO | 0197808 A1 | 12/2001 |
| WO | 0202560 A2 | 1/2002 |
| WO | 0214271 A1 | 2/2002 |
| WO | 0224698 A1 | 3/2002 |
| WO | 02053516 A2 | 7/2002 |
| WO | 02068420 A1 | 9/2002 |
| WO | 03000241 A2 | 1/2003 |
| WO | 03002531 A2 | 1/2003 |
| WO | 03004496 A1 | 1/2003 |
| WO | 03024965 A2 | 3/2003 |
| WO | 03033686 A2 | 4/2003 |
| WO | 03034944 A1 | 5/2003 |
| WO | 03037327 A1 | 5/2003 |
| WO | 03053929 A1 | 7/2003 |
| WO | 03055881 A1 | 7/2003 |
| WO | 03057200 A2 | 7/2003 |
| WO | 03064454 A1 | 8/2003 |
| WO | 03088900 A2 | 10/2003 |
| WO | 03094909 A2 | 11/2003 |
| WO | 03099279 A1 | 12/2003 |
| WO | 03099836 A1 | 12/2003 |
| WO | 03104229 A1 | 12/2003 |
| WO | 03106428 A1 | 12/2003 |
| WO | 2004002924 A1 | 1/2004 |
| WO | 2004011416 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004041820 A1 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A | 8/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007647 A1 | 1/2005 |
| WO | 2005007658 A2 | 1/2005 |
| WO | 2005012288 A1 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006083491 A2 | 8/2006 |
| WO | 2006135693 A2 | 12/2006 |
| WO | 2006137085 A2 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 2007033350 A1 | 3/2007 |
| WO | 2007035355 A2 | 3/2007 |
| WO | 2007035665 A1 | 3/2007 |
| WO | 2007041053 A2 | 4/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |

(56) References Cited

FOREIGN PATENT DOCUMENTS

| | | |
|---|---|---|
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009064399 A1 | 5/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A1 | 4/2010 |
| WO | 2010072776 A1 | 7/2010 |
| WO | 2010079197 A1 | 7/2010 |
| WO | 2010/092124 A1 | 8/2010 |
| WO | 2010086411 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010147768 A1 | 12/2010 |
| WO | 2011011541 A1 | 1/2011 |
| WO | 2011039337 A1 | 4/2011 |
| WO | 2011039367 A2 | 4/2011 |
| WO | 2011064352 A1 | 6/2011 |
| WO | 2011113947 A1 | 9/2011 |
| WO | 2011138380 A1 | 11/2011 |
| WO | 2011138421 A1 | 11/2011 |
| WO | 2011161161 A1 | 12/2011 |
| WO | 2011163206 A2 | 12/2011 |
| WO | 2012031124 A2 | 3/2012 |
| WO | 2012065993 A1 | 5/2012 |
| WO | 2012106303 A1 | 8/2012 |
| WO | 2012120040 A1 | 9/2012 |
| WO | 2013098372 A1 | 7/2013 |
| WO | 2013103629 A1 | 7/2013 |
| WO | 2013171167 A1 | 11/2013 |
| WO | 2013174768 A1 | 11/2013 |

OTHER PUBLICATIONS

Clinical Trial Identifier NCT00954447, "Efficacy and Safety of Linagliptin in Combination with Insulin in Patients With Type 2 Diabetes" update of Jun. 14, 2010, http://clinicaltrials.gov/archive/NCT00954447/2010_06_14.*
Deacon et al., "Linagliptin, a xanthine-based dipeptidyl peptidease-4 inhibitor with an unusual profile for the treatment of type 2 diabetes," Expert Opin. Investig. Drugs 19:133-140 (Jan. 2010).*
Sarafidis et al., "Cardiometabolic syndrome and chronic kidney disease: what is the link", JCMS 1:58-65 (2006).*
Holman, et al., "Addition of biphasic, prandial, or basal insulin to oral therapy in type 2 diabetes," N. Eng. J. Med. 357:1716-30 (2007).*
Wertheimer, et al., "Drug delivery systems improve pharmaceutical profile and facilitate medication adherence," Adv. Therapy 22:559-577 (2005).*
Gomez-Perez et al., "Insulin therapy: current alternatives," Arch. Med. Res. 36:258-272 (2005).*
Clinical Trial Identifier NCT00954447, "Efficacy and Safety of Linagliptin in Combination with Insulin in Patients with Type 2 Diabetes" update of Jun. 14, 2010, http://clinicaltrials.gov/archive/NCT00954447/2010 06 14, accessed Jul. 18, 2013.*
Ahren, BO, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Bastin, R.J. et al., "Salt Selection and Optimization Procedures for Pharmaceutical New Chemical Entities". Organic Process Research and Development, 2000, vol. 4, p. 427-435.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Demuth, H-U. et al., "Type 2 diabetes—Therapy with dipeptidyl peptidase IV inhibitors". Biochimica et Biophysica Acta, vol. 1751(1), 2005, p. 33-44.
European Search Report for EP 08 15 9141 mailed Apr. 6, 2009 (European counterpart of U.S. Appl. No. 12/143,128).
Gallwitz, B. "Sitagliptin with Metformin: Profile of a Combination for the Treatment of Type 2 Diabetes". Drugs of Today, Oct. 2007, 43(10), p. 681-689.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
Hermann, Robert, et al; Lack of Association of PAX4 Gene with Type 1 Diabetes in the Hungarian Populations; Diabetes (2005) vol. 54 pp. 2816-2819.
Hunziker, D. et al, "Inhibitors of DPP IV-recent advances and structural views", Current Topics in Medicinal Chemistry, 2005, vol. 5 issue 16, pp. 1623-1637.
International Search Report and Written Opinion for PCT/EP2011/060449 mailed Sep. 27, 2011.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
Kibbe, Editor. Handbook of Pharmaceuticals Excipiets, Third Edition, Copovidon—pp. 196-197, Date of Revision: Dec. 16, 2008. Mannitol—pp. 424-425, Date of Revision: Feb. 19, 2009.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
Levien,T.L. et al, "New drugs in development for the treatment of diabetes", Diabetes Spectrum, American Diabetes Association, US, vol. 22, No. 2, Jan. 1, 2009, pp. 92-106.
Mayo Clinic Staff: "Nonalchoholic fatty liver disease: Prevention"[retrieved on Nov. 30, 2012]. retrieved from the Internet: ,URL: http://www.mayoclinic.com/health/nonalcoholic-fatty-liver-disease/DS00577DSECTION=prevention>.
Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.
Rosenstock, J. et al., "Alogliptin added to insulin therapy in patients with type 2 diabetes reduces HbA1c without causing weight gain or

(56) References Cited

OTHER PUBLICATIONS increased hypoglycaemia". Diabetes, Obesity and Metabolishm, Dec. 2009, vol. 11. No. 12, p. 1145-1152.

Shanks, N. et al., Are animal models predictive for humans?, PEHM, Philosophy, Ethics, and Humanaities in Medicine, 4(2), 2009, 1-20.

Sune Negre, J. M. "New Galenic Contributions to Administration Forms". Continued Training for Hospital Pharmacists 3.2. [retrieved on Feb. 23, 2011]. Retrieved from the internet <http://www.ub.es/legmh/capitols/sunyenegre.pdf>.

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

Abstract in English for German DE2205815, 1972.

Abstract in English for German EP0023032, 1981.

Abstract in English, for KR20070111099, Nov. 11, 2007.

Ahren B: "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.

Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.

Augusti, D.V. et al., "Quantitative determinatio of the enantiomeric composition of thalidomide solutions by electrospray ionizatio tandem mass spectrometry". Chem Comm, 2002, p. 2242-2243.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Aulinger, B.A. et al., "Ex-4 and the DPP-IV Inhibitor Vildagliptin have Additive Effects to Suppress Food Intake in Rodents". Abstract No. 1545-P, 2008.

Balaban, Y.H.et al., "Dipeptidyl peptidase IV (DDP IV) in NASH patients" Annals of Hepatology, vol. 6, No. 4, Oct. 1, 2007, pp. 242-250, abstract.

Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Beljean-Leymarie et al., Hydrazines et hydrazones heterocycliques. IV. Syntheses de derives de l'hydrazine dans la serie des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 18-193.

Brittain, H.G., "Methods for the Characterization of Polymorphs: X-Ray Powder Diffraction," Polymorphism in Pharmaceutical Solids, 1999, p. 235-238.

Bundgaard, H. "Design of prodrugs: Bioreversible derivatives for various functional groups and chemical entities". Royal Danish School of Pharmacy, 1985, p. 1-92.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Chemical Abstract. EP412358, 1991:185517, Findeisen.

Chemical Abstract: FR2707641, 1995:543545, Dodey.

Chemical Abstract: No. 211513-37-0-Dalcetrapib. "Propanethioic acid, 2-methyl-,S-(2-[[[1-(2-ethylbutyl)cyclohexyl}carbonyl}amino}pheyl}ester". Formula: C23 H35 N O2 S. American Chemical Society. Sep. 20, 1998.

Chemical Abstract: No. 875446-37-0-Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 N O3. American Chemical Society, Feb. 28, 2006.

Chemical Abstracts Accession No. 106:95577 Romanenko et al., "Synthesis and Biological Activity of 3-Methyl, 7-or 8-alkyl-7,8dialkyl, heterocyclic, and cyclohexylaminoxanthines," Zaporozh. Med. Institute (1986).

Chemical Abstracts Accession No. 1987:95577: Abstract of Romanenko et al., "Synthesis and biological activity of 3-methyl, 7-or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.

Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT0060125/2008_01_25 [retrieved on Feb. 27, 2009].

Clinical Trials. NCT00622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.

Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.

Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.

Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.

Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.

Clinical Trials: NCT00798161. "Safety and efficacy of BI 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.

Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.

Conarello, S.L. et al., "Mice lacking dipeptidyl peptidase IV are protected against obesity and insulin resistance". PNAS, May 27, 2003, vol. 100, No. 11, p. 6825-6830.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

(56) References Cited

OTHER PUBLICATIONS

Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.

DeMeester, I. et al.; "CD26, let it cut or cut it down", Review: Immunology Today; Aug. 1999, vol. 20, No. 8 pp. 367-375

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Eckhardt Matthias et al: 8-(3-(R)-aminopiperidin-1-yl)-7-but-2-ynyl-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 11, 2008, pp. 3158-3162, XP022711188

Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.

Gallwitz, B. et al., "Saxagliptin, a dipeptidyl peptidase IV inhibitor for the treatment of type 2 diabetes". IDRUGS, vol. 11, No. 12, Dec. 2008, p. 906-917.

Garber, A.J. et al., "Update: Vildaglitin for the treatment of Type 2 diabetes" Expert Opinion on Investigational Drugs, 200801GB, vol. 17, No. 1, Jan. 2008, p. 105-113.

Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.

Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.

Giron, D.; Thermal Analysis and Calorimetric Methods in the Characterisation of Polymorphs and Solvates; Thermochimica Acta (1995) Vol. 248 pp. 1-59.

Graefe-Mody et al., "The novel DPP-4 inhibitor" Diabetes, (online) 2008, XP002561421 http://professional.diabetes.org/content/posters/2008/p553-p.pdf.

Greene, T.W, et al., "Protection for the Amino Group". Protective Groups in Organic Synthesis, 3rd edition, 1999, p. 494-653.

Gwaltney, S. "Medicinal Chemistry Approaches to the Inhibition of Dipeptidyl Peptidase IV", Current Topics in Medicinal Chemistry, 2008, 8, p. 1545-1552.

He, Y.L. et al., "The influence of hepatic impariment on the pharmacokinetics f the dipeptidyl peptidase IV (DPP-4) inhibitor vildagliptin" European Journal of Clinical Pharmacology, vol. 63, No. 7, May 8, 2007, p. 677-686.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

Januvia; Patient Information; 2010.

Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.

Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

March, J. "Advanced Organic Chemistry: Reactions, Mechanisms, and Structure". Fourth Edition, 1992, pp. 652-653.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.

O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.

Patani George A. et al.: "Bioisoterism : A Rational Approach in Drug Design", Chemical Reviews, 1996, vol. 96, No. 8, pp. 3147-3176.

Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.

Pospisilik, et al; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.

Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.

Rhee et al.: "Nitrogen-15-Labeled Deoxynucleosides. 3. Synthesis of [3-15N]-2'-Deoxyadenosine" J. Am. Chem. Soc. 1990, 112, 8174-8175.

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.

Salomon, J., et al; Ultraviolet and g-Ray-Induced Reactions of Nucleic Acid Constituents. Reactions of Purines with Amines; Photochemistry and Photobiology (1974) vol. 19 pp. 21-27.

Sathananthan, A., et al., "Personalized pharmacotherapy for type 2 diabetes mellitus". Personalized Medicine 2009 Future Medicine Ltd, vol. 6, No. 4, Jul. 2009, p. 417-422.

Sauer, R, et al. "Water-soluble phosphate prodrugs of 1-Propargyl-7-styryixanthine derivatives, A2A-selective adenosine receptor antagonists". Journal Med. Chem., vol. 43, issue 3, Jan. 2000, p. 440-448.

Schwartz, M. S. et al., "Type 2 Diabetes Mellitus in Childhood: Obesity and Insulin Resistance". JAOA Review Article, vol. 108, No. 9, Sep. 2008, p. 518.

Scientific Discussion: "Eucreas, Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Stahl, P.H. "Handbook of Pharmaceutical Salts". C.G. Wermuth, Wiley-VCH, 2002, p. 61.

Tamm, E, et al., "Double-blind study comparing the immunogenicity of a licensed DTwPHib-CRM197 conjugate vaccine (Quattvaxem

(56) References Cited

OTHER PUBLICATIONS

TM) with three investigational, liquid formulations using lower doses of Hib-CRM197 conjugate". Science Direct, Vaccine, Feb. 2005, vol. 23, No. 14, p. 1715-1719.

Tanaka, S.. et al; "Suppression of Arthritis by the Inhibitors of Dipeptidyl Peptidase IV," In. J. Innunopharmac., vol. 19, No. 1, pp. 15-24, 1997.

Thomas, L, et al: "BI 1356, a novel and selective xanthine beased DDP-IV inhibitor, exhibits a superior profile when compared to sitagliptin and vildagliptin." Diabetologoa, vol. 50, No. Suppl. 1, Sep. 2007, p. S363.

Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics, vol. 325, No. 1, pp. 175-182, 2008.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

White, J.R., "Dipeptidyl Peptidase-IV Inhibitors: Phamacological Profile and Clinical Use". Clinical Diabetes, vol. 26, 2008, p. 53-57.

Wikipedia, Annulation. Jun. 23, 2008, http://en.wikipedia.org/wiki/Annelation.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

Wolff, M.E.: "Burger's Medicinal Chemistry and Drug Discovery" Fifth Edition, vol. 1: Principles and Practice, pp. 975-977, 1994, John Wiley & Sons, Inc.

World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.

X-Ray Diffraction. The United States Pharmacopeia, 2002, USP 25 NF20, p. 2088-2089.

Yasuda, et al. "E3024 3-but-2-ynyl-5-methyl-2-piperazin-1-y1-3,5-dihydro-4H-imidazol [4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.

Yoshikawa, Seiji et al.: Chemical Abstract of Japanese Patent No. WO 2003/104229 Preparation of purinone derivatives as dipeptidylpeptidase IV (DPP-IV) inhibitors, 2003.

Zejc, Alfred, et al; "Badania Nad Piperazynowymi Pochodnymi Dwumetyloksantyn" Acta Polon Pharm, XXXV (1976) Nr. 4 pp. 417-421.

Zhong, Qing et al; "Glucose-dependent insulinotropic peptide stimulates proliferation and TGF-? release from MG-63 cells," Peptides 24 (2003) 611-616.

Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.

International Search Report and Written Opinion for PCT/EP2011/057163 mailed Jun. 27, 2011.

Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.

American Diabetes Association, "Standards of Medical Care in Diabetes—2008." Diabetes Care, Jan. 2008, vol. 31, Supplement 1, pp. S12-S54.

Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.

Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.

Eucreas Scientific Discussion, 2007, p. 1-27, www.emea.europa.eu/humandocs/PD/Fs/EPAR/eucreas/H-807-en6.pdf, Anonymous.

Anonymous, Clinicaltrials.gov, 2008, No. NCT00622284, "Efficacy and Safety of BI 1356 in combination with metformin in patients with type 2 diabetes" p. 1-5.

Pratley, R. et al., "Inhibition of DPP-4: a new therapeutic approach for the treatment of type 2 diabetes." Current Medical Research and Opinion, 2007, vol. 23, No. 4, pp. 919-931.

Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.

Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.

Chemical Abstracts Service, Database Accession No. No. RN 668270-12-01, 2004, "1H-Purine-2,6-dione, 8-[(3R)-3-amino-1-piperidinyl]-7-(2-butyn-1-yl)-3,7-dihydro-3-methyl-1-[(4-methyl-2-quinazolinyl)methyl]".

Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.

Balbach, S. et al., Pharmaceutical evaluation of early development candidates "the 100 mg-approach." International Journal of Pharmaceutics, 2004, vol. 275, pp. 1-12.

Singhal, D. et al., "Drug polymorphism and dosage form design: a practical perspective." Advanced Drug Delivery Reviews, 2004, vol. 56, pp. 335-347.

Hilfiker, R. et al., "Relevance of Solid-state Properties for Pharmaceutical Products." Polymorphism in the Pharmaceutical Industry, 2006, Chapter 1, pp. 1-19.

Dunitz, J. et al., "Disappearing Polymorphs." Acc. Chem. Res. 1995, vol. 28, No. 4, pp. 193-200.

Byrn, Stephen R. "Solid-State Chemistry of Drugs." Academic Press, 1982, pp. 1-27.

Bernstein, Joel "Polymorphism in Molecular Crystals." Oxford University Press, 2002, p. 9.

Third Party Observation for application No. EP20070728655, May 13, 2013.

Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.

Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.

Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.

Fukushima et al., Drug for Treating Type II Diabetes (6), "action-mechanism of DPP-IV inhibitor and the availability thereof" Mebio, 2009, vol. 26, No. 8, p. 50-58.

(56) References Cited

OTHER PUBLICATIONS eMedicine Health, "Diabetes Causes." Retrieved from internet on Aug. 22, 2013. <http://www.onhealth.com/diabetes_health/page3.htm#diabetes_causes>.
International Search Report for PCT/EP2007/054204 mailed Mar. 8, 2007.
Lovshin, J.A. et al., "Incretin-based therapies for type 2 diabetes mellitus." Nature Reviews Endocrinology, 2009, vol. 5, pp. 262-269.
International Search Report and Written Opinion for PCT/EP2011/057256 dated Jul. 22, 2011.
International Search Report and Written Opinion for PCT/EP2013/060312 mailed on Sep. 4, 2013.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Headland, K. et al., "The Effect of Combination Linagliptin and Voglibose on Glucose Control and Body Weight." 73rd Annual Meeting Science Session, ADA, Chicago, Jun. 21, 2013.
Nielsen, L., "Incretin Mimetics and DPP-IV Inhibitors for the Treatment of Type 2 Diabetes." DDT, 2005, vol. 10, No. 10, pp. 703-710.
Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.
International Search Report and Written Opinion for PCT/EP2013/059828 mailed Aug. 6, 2013.
Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.
Chaykovska, L. et al., "Effects of DPP-4 Inhibitors on the Heart in a Rat Model of Uremic Cardiomyopathy." www.plosone.org, 2011, vol. 6, No. 11, p. e27861.
Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.
Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct. 2012, http://www.abstractsonline.com/Plan/ViewAbstract.aspx?sKey=8b8817b9-ge98-4695-b9af-b6878e96a921&cKey=421edb9c-b948-48f8-b282-8e61245561d5&mKey={2DBFCAF7-1539-42D5-8 DDA-8A94ABB889E8}.
International Search Report and Written Opinion for PCT/EP2013/059831 mailed on Aug. 9, 2013.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012, http://www.abstractsonline.com/Plan/ViewAbstract.aspx?sKey=Ob0017b9-ge90-4695-b9af-b6870e96a921&cKey=8eff47ae-db49-4c36-al42-848ac068c405&mKey={2DBFCAF7-1539-42D5-8DDA-OA94ABB089E8}.
Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013 http://www.abstractsonline.com/Plan/ViewAbstract.aspx?sKey=e68ac573-fe45-4c2f-9485-6278854fc18b&cKey=3c387569-84de-4f8c-b825-b358df91ca64&mKey={89918D6D-3818-4EA9-9D4F-711F98A7AE5D}.
Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www. abstractsonline.com, Jun. 10, 2012, XP-002708003.
International Search Report and Written Opinion for PCT/EP2013/060311 mailed Aug. 9, 2013.
Adebowale, K.O. et al., "Modification and properties of African yam bean (Sphenostylis stenocarpa Hochst. Ex A. Rich.) Harms starch I: Heat moisture treatments and annealing." Food Hydrocolloids, 2009, vol. 23, No. 7, pp. 1947-1957.
International Search Report and Written Opinion for PCT/EP2013/070978 mailed on Oct. 31, 2013.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Abstract in English for JP 2002/348279, Dec. 4, 2002.
Abstract in English for JP 2003/286287, Oct. 10, 2003.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Lee Jones, K. et al., "Effect of Metformin in Pediatric Patients With Type 2 Diabetes." Diabetes Care, 2002, vol. 25, No. 1, pp. 89-94.
Anstee, Quentin M. et al. "Mouse models in non-alchoholic fatty liver disease and steatohepatitis research" (2006) International Journal of Expermental Pathology, vol. 87, pp. 1-16.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Clinical Trial NCT00622284 (published online at clinicaltrials.gov on Feb. 22, 2008).
Gallwitz, B. et al., DPP IV inhibitors for the Treatment of Type 2 Diabetes; Diabetes Frontier (2007) vol. 18, No. 6 pp. 636-642.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Hayashi, Michio., "Recipe for Oral Hypoglycemic Agents to Pathological Condition" Pharmacy (2006) vol. 57, No. 9 pp. 2735-2739.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
Kharkevich, D. A., "Educational Literature" Pharmacology (1987) Third Edition, Meditsina Press, Moscow pp. 47-48.
Komori, Kiyoshi., "Treatment of Diabetes in Patients for Whom Metforming Treatment is Not Appropriate" Modern Physician (2008) vol. 28, No. 2 pp. 163-165.
Matsumiya, Teruhiko, et al., "Therapeutic Drugs for Clinicians" Diagnosis and Treatment (2008) vol. 96, No. 2 pp. 389-390.
Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on

(56) References Cited

OTHER PUBLICATIONS

Metformin alone: A Randomized, Double-Blind, Non-Inferiority Trial." Diabetes Obesity and Metabolism, 2007, vol. 9, No. 2, pp. 194-205.
Shintani, Maki, et al., "Insulin Resistance and Genes" Circulatory Sciences (1997) vol. 17, No. 12 pp. 1186-1188.
Tounyoubyou, "Symposium-19: Future Perspectives on Incretion Therapy in Diabetes." 2008, vol. 51, Suppl. 1, p. S-71, S19-2.
Plummer, C.J.G. et al., "The Effect of Melting Point Distributions on DSC Melting Peaks." Polymer Bulletin, 1996, vol. 36, pp. 355-360.
Office Action for U.S. Appl. No. 10/695,597 mailed May 2, 2008.
Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.
Tribulova, N. et al. "Chronic Disturbances in NO Production Results in Histochemical and Subcellular Alterations of the Rat Heart." Physiol. Res., 2000, vol. 49, No. 1, pp. 77-88.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.
Hu, Y. et al., "Synthesis and Structure-activity Relationship of N-alkyl Gly-boro-Pro Inhibitors of DPP4, FAP and DPP7." Bioorganic & Medicinal Chemistry Letters 15, 2005, pp. 4239-4242.
Tradjenta, Highlights of Prescribing Information (revised Sep. 2012).
Inukai, T., "Treatment of Diabetes in Patients for Whom Metformin Treatment is Not Appropriate." Modern Physician, 2008, vol. 28, No. 2, pp. 163-165.
Gennaro, Alfonso R., Remington Farmacia, 19th Edition, Spanish copy, 1995, p. 2470.
Berge, S. et al., "Pharmaceutical Salts." Journal of Pharmaceutical Sciences, 1977, vol. 66, No. 1, pp. 1-19.
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Nihon Ijinpo, Japan Medicinal Journal, 2001, No. 4032, p. 137.
Definition of "prevent", e-dictionary, Aug. 15, 2013, http://dictionary.reference.com/browse/prevent.
Medline Plus, "Obesity" 2013, Retrieved from internet on Aug. 22, 2013, http://www.nlm.nih.gov/medlineplus/obesity.html.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Ferry, Robert Jr., "Diabetes Causes." eMedicine Health, MedicineNet.com, 2013, Retrieved from internet on Aug. 22, 2013, http://www.onhealth.com/diabetes_health/page3.htm#diabetes_causes.
United Healthcare, "Diabetes." Retrieved from internet on Aug. 22, 2013, http://www.uhc.com/source4women/health_topics/diabetesirelatedinformation/dOf0417b073bf11OVgnVCM1000002f1Ob1Oa_. htm.
Florez, J. et al. "TCF7L2 Polymorphisms and Progression to Diabetes in the Diabetes Prevention Program." The New England Journal of Medicine, 2006, vol. 355, No. 3, pp. 241-250.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Diabetesincontrol.com "EASD: Eucreas, a Combination of Galvus and Metformin, Recommended for Approval." Diabetes in Control.com, Sep. 25, 2007, Retrieved from internet on Nov. 30, 2012, http://www.diabetesincontrol.com/articles/53-diabetes-news/5145.
Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.
Drucker, et al.., The incretin system:glucagon-like peptide-1 receptor agonists and dipeptidyl peptidase-4 inhibitors in type 2 diabetes. Lancet, 2006, 368: 1696-1705.
Horsford, E. N. "On the source of free hydrochloric acid in the gastric juice." Proceedings of the Royal Society of London, Published in 1868-1869, vol. 17, pp. 391-395.
Halimi, et al., "Combination treatment in the management of type 2 diabetes focus on vildagliptin and metformin as a single tablet", Vascualr Health and Risk Management, 2008, 4(3) p. 481-492.
Nielsen, L., "Incretin mimetics and DPP-IV inhibitors for the treatment of type 2 diabetes." Drug Discovery Today, 2005, vol. 10, No. 10, pp. 703-710.
Sarafidis, P. et al., "Cardiometabolic Syndrome and Chronic Kidney Disease: What is the link?"JCMS 2006, 1: p. 58-65.
Kim, Kwang-Rok et al., "KR-62436, 6-{2-{2-(5-cyano4,5-dihydropyrazol-1-yl)-2-oxoethylamino}ethylamino}nicotinonitrile, is a novel dipeptidyl peptidase-IV (DDP-IV) inhibitor with anti-hyperglycemic activity" European Journal of Pharmacology 518, 2005, p. 63-70.
Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Dave, Rutesh H. "Overview of pharmaceutical excipients used in tablets and capsules." Drug Topics, Oct. 24, 2008.
Abstract in English for German DE10109021, 2002.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Glucotrol XL (glipizide), package insert, Pfizer, Apr. 1, 2002.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Thornber, C.W., "Isosterism and Molecular Modification in Drug Design." Chemical Society Reviews, 1979, pp. 563-580.
ChemGaroo, "Leaving Group." 1999, Retrieved online: http://www.chemgapedia.de/vsengine/vlu/vsc/en/ch/12/oc/vluorganik/substitution/sn _ 2/sn 2.vlu/Page/vsc/en/ch/12/oc/substitution/sn _ 2/abgangsgrupen/abgangsgruppe.vscml.html.
Silverman, G. et al., "Handbook of Grignard Reagents." 1996, Retrieved online: <http://books.google.com/books?id=82CaxfY-uNkC&printsec=frontcover &dq=intitle:Handbook+intitle:of+intitle:Grignard+intitle:Reagents &hl=en&sa=X&ei=g06GU5SdOKngsATphYCgCg &ved=0CDYQ6AEwAA#v=onepage&q&f=false>.
John Hopkins Children's Center, "Liver Disorders and Diseases." Retrieved online May 26, 2014 <http://www.hopkinschildrens.org/non-alcoholic-fatty-liver-disease.aspx>.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Sortino, M.A. et al., "Linagliptin: a thorough characterization beyond its clinical efficacy." Frontiers in Endocrinology, 2013, vol. 4, Article 16, pp. 1-9.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 1, pp. 1-10.

(56) References Cited

OTHER PUBLICATIONS

Haluzik, M. et al., "Renal Effects of DPP-4 Inhibitors: A Focus on Microalbuminuria." International Journal of Endocrinology, 2013, vol. 35, No. 6, pp. 1-7.
International Search Report and Written Opinion for PCT/EP2012/077024 mailed Feb. 19, 2013.
Rosenbloom, et al., "Type 2 Diabetes mellitus in the child and adolescent", Pediatric Diabetes, 2008, p. 512-526.
International Search Report for PCT/EP2013/060309 mailed Aug. 9, 2013.
Partial International Search Report for PCT/EP2014/060160, mailing date Jun. 30, 2014.
International Search Report and Written Opinion for PCT/EP2014/055113 mailed May 16, 2014.
Iwamoto, "Insulin Glargine", Nippon Rinsho, 60:503-515 (2002).
Prescribing Information, Package insert for Leprinton tablets 100mg, Manufacturer: Tatsumi Kagaku Co., Ltd., Mar. 2003, pp. 1-3.
Hashida, Mitsuru, "Strategies for designing and developing oral administration formulations." Yakuji-Jiho, Inc., 1995, pp. 50-51.
Rask-Madsen, C. et al., "Podocytes lose their footing." Nature, 2010, vol. 468, pp. 42-44.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Nielsen, "Incretin mimetics and DPP-IV inhibitors for the treatment of type 2 diabetes," Drug Discovery Today 10(10):703-710(2005).
Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.
Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.
International Search Report for PCT/EP2013/070979 mailed Nov. 26, 2013.
McNay, David E.G. et al., "High fat diet causes rebound weight gain." Molecular Metabolism, 2013, vol. 2, pp. 103-108.
Radermecker, Regis et al., "Lipodystrophy Reactions to Insulin." American Journal of Clinical Dermatology, 2007, vol. 8, pp. 21-28.
Sheperd, Todd M. et al., "Efective management of obesity." The Journal of Family Practice, 2003, vol. 52, No. 1, pp. 34-42.
Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.
Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.
Lyssenko, V. et al., "Mechanisms by which common variants in the TCF7L2 gene increase risk of type 2 diabetes." The Journal of Clinical Investigation, 2007, vol. 117, No. 8, pp. 2155-2163.
Pearson, E. R. et al., "Variation in TCF7L2 Influences Therapeutic Response to Sulfonylureas." Diabetes, 2007, vol. 56, pp. 2178-2182.
Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Tadayyon, M. et al., "Insulin sensitisation in the treatment of Type 2 diabetes." Expert Opinion Investigative Drugs, 2003, vol. 12, No. 3, pp. 307-324.
Hocher, B. et al., "The novel DPP-4 inhibitors linagliptin and BI 14361 reduce infarct size after myocardial ischemial/reperfusion in rats." International Journal of Cardiology, 2013, vol. 167, pp. 87-93.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Klein, T. et al., "Linagliptin alleviates hepatic steatosis and inflammation in a mouse model of non-alcoholic steatohepatitis." Medical Molecular Morphology, 2014, vol. 47, pp. 137-149.
Standl, E. et al., "Diabetes and the Heart." Diabetes Guidelines (DDG), 2002, pp. 1-25.
National Program for Care Guidelines, "Type 2 Diabetes mellitus." 2002, First Edition, pp. 1-50.
Lakatos, P. L. et al., "Elevated serum dipeptidyl peptidase IV (CD26, EC 3.4.14.5) activity in patients with primary biliary cirrhosis." Journal of Hepatol, 1999, vol. 30, p. 740.
Baetta, R. et al., "Pharmacology of Dipeptidyl Peptidase-4 Inhibitors." Drugs, 2011, vol. 71, No. 11, pp. 1441-1467.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Naik, R. et al., "Latent Autoimmune Diabetes in Adults." The Journal of Clinical Endocrinology and Metabolism, 2009, vol. 94, No. 12, pp. 4635-4644.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Isomaa, B. et al., "Cardiovascular Morbidity and Mortality Associated With the Metabolic Syndrome." Diabetes Care, 2001, vol. 24, No. 4, pp. 683-689.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.
Crowe, E. et al., "Early identification and management of chronic kidney disease: summary of NICE guidance." British Medical Journal, 2008, vol. 337, pp. 812-815.
Hull, R. et al., "Nephrotic syndrome in adults." British Medical Journal, 2008, vol. 336, pp. 1185-1190.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Blech, et al, Drug Metabolism and Deposition, "The Metabolism and Disposition of the Oral Dipeptidyl Peptidase-4 Inhibitor, Linagliptin, in Humans", 2009, vol. 38, No. 4, p. 667-678.
Greischel, et al., Drug Metabolism and Deposition, "The Dipeptidyl Peptidase-4 Inhibitor Linagliptin Exhibits Time-and Dpse-Dependent Localization in Kidney, Liver, and Intestine after Intravenous Dosing: Results from High Resolution Autoradiography in Rats", 2010, vol. 38, No. 9, p. 1443-1448.
Cheon, et al., Biochemical Pharmacology, "Inhibition of dipeptidyl IV by novel inhibitors with pyrazolidine scaffold", 2005, vol. 70, p. 22-29.
International Search Report and Written Opinion for PCT/EP2015/054114 mailed May 12, 2015.
Konstantinou, D. M. et al., "Pathophysiology-based novel pharmacotherapy for heart failure with preserved ejection fraction." Pharmacology & Therapeutics, 2013, vol. 140, No. 2, pp. 156-166.
Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.
Zhimei, Xiao et al., "Study progression of oral drugs for treatment of type II diabetes." Drug Evaluation, 2004, vol. 1, No. 2, pp. 138-143.
Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.

* cited by examiner

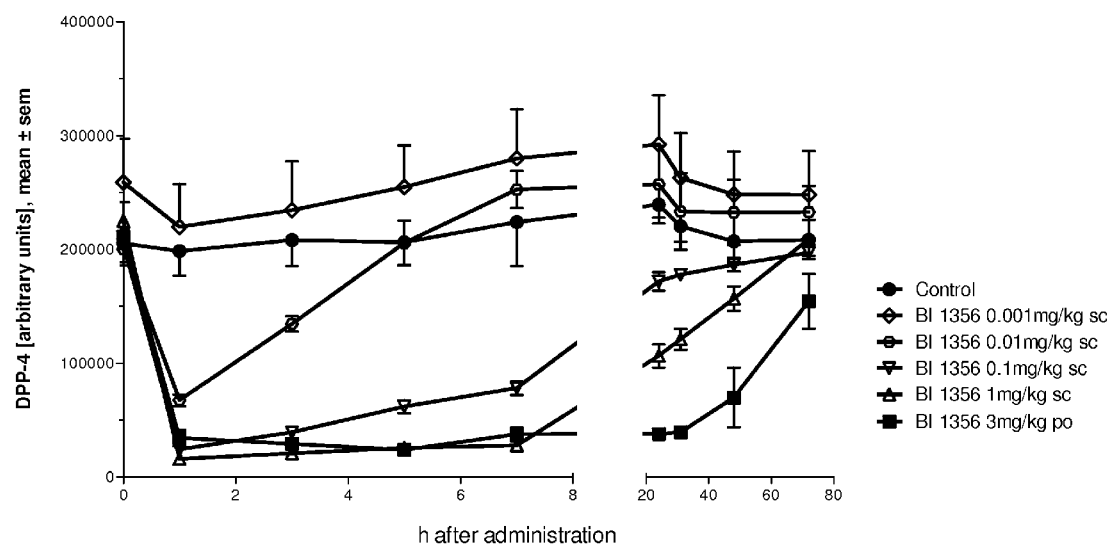

DIABETES THERAPY

FIELD OF THE INVENTION

The present invention relates methods for treating and/or preventing metabolic diseases, especially type 2 diabetes mellitus and/or conditions related thereto (e.g. diabetic complications) comprising the combined administration of long-acting insulin (such as e.g. insulin glargine or insulin detemir) and a certain DPP-4 inhibitor, to pharmaceutical compositions and combinations comprising such active components, and to certain therapeutic uses thereof.

BACKGROUND OF THE INVENTION

Type 2 diabetes mellitus is a common chronic and progressive disease arising from a complex pathophysiology involving the dual endocrine effects of insulin resistance and impaired insulin secretion with the consequence not meeting the required demands to maintain plasma glucose levels in the normal range. This leads to chronic hyperglycaemia and its associated micro- and macrovascular complications or chronic damages, such as e.g. diabetic nephropathy, retinopathy or neuropathy, or macrovascular (e.g. cardio- or cerebro-vascular) complications. The vascular disease component plays a significant role, but is not the only factor in the spectrum of diabetes associated disorders. The high frequency of complications leads to a significant reduction of life expectancy. Diabetes is currently the most frequent cause of adult-onset loss of vision, renal failure, and amputation in the Industrialised World because of diabetes induced complications and is associated with a two to five fold increase in cardiovascular disease risk.

The treatment of type 2 diabetes typically begins with diet and exercise, followed by oral antidiabetic monotherapy, and although conventional monotherapy may initially control blood glucose in some patients, it is however associated with a high secondary failure rate. The limitations of single-agent therapy for maintaining glycemic control may be overcome, at least in some patients, and for a limited period of time by combining multiple drugs to achieve reductions in blood glucose that cannot be sustained during long-term therapy with single agents. Available data support the conclusion that in most patients with type 2 diabetes current monotherapy will fail and treatment with multiple drugs will be required.

But, because type 2 diabetes is a progressive disease, even patients with good initial responses to conventional combination therapy will eventually require an increase of the dosage or further treatment with insulin because the blood glucose level is very difficult to maintain stable for a long period of time. Although existing combination therapy has the potential to enhance glycemic control, it is not without limitations (especially with regard to long term efficacy). Further, traditional therapies may show an increased risk for side effects, such as hypoglycemia or weight gain, which may compromise their efficacy and acceptability. Thus, for many patients, these existing drug therapies result in progressive deterioration in metabolic control despite treatment and do not sufficiently control metabolic status especially over long-term and thus fail to achieve and to maintain glycemic control in advanced or late stage type 2 diabetes, including diabetes with inadequate glycemic control despite conventional oral or non-oral antidiabetic medication.

Therefore, although intensive treatment of hyperglycemia can reduce the incidence of chronic damages, many patients with type 2 diabetes remain inadequately treated, partly because of limitations in long term efficacy, tolerability and dosing inconvenience of conventional antihyperglycemic therapies.

This high incidence of therapeutic failure is a major contributor to the high rate of long-term hyperglycemia-associated complications or chronic damages (including micro- and macrovascular complications such as e.g. diabetic nephropathy, retinopathy or neuropathy, or cerebro- or cardio-vascular complications such as e.g. myocardial infarction, stroke or death) in patients with type 2 diabetes.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides and α-glucosidase inhibitors.

Non-oral (typically injected) antidiabetic drugs conventionally used in therapy (such as e.g. first- or second-line, and/or mono- or (initial or add-on) combination therapy) include, without being restricted thereto, GLP-1 or GLP-1 analogues, and insulin or insulin analogues.

However, the use of these conventional antidiabetic or antihyperglycemic agents can be associated with various adverse effects. For example, metformin can be associated with lactic acidosis or gastrointestinal side effects; sulfonylureas, glinides and insulin or insulin analogues can be associated with hypoglycemia and weight gain; thiazolidinediones can be associated with edema, bone fracture, weight gain and heart failure/cardiac effects; and alpha-glucosidase blockers and GLP-1 or GLP-1 analogues can be associated with gastrointestinal adverse effects (e.g. dyspepsia, flatulence or diarrhea, or nausea or vomiting).

Therefore, it remains a need in the art to provide efficacious, safe and tolerable antidiabetic therapies.

Further, within the therapy of type 2 diabetes, it is a need for treating the condition effectively, avoiding the complications inherent to the condition, and delaying disease progression.

Further, within the therapy of type 2 diabetes, it is a need for sustained improvements in diabetic phenotype, glycemic and/or metabolic control, and/or (blood) glucose profile (preferably over long-term and/or during chronic treatment).

Furthermore, it remains a need that antidiabetic treatments not only prevent the long-term complications often found in advanced stages of diabetes disease, but also are a therapeutic option in those diabetes patients who have developed or are at risk of developing complications, such as renal impairment.

Moreover, it remains a need to provide prevention or reduction of risk for adverse effects associated with conventional antidiabetic therapies.

SUMMARY OF THE INVENTION

In one embodiment, the present invention relates methods for treating and/or preventing metabolic diseases, especially type 2 diabetes mellitus and/or conditions related thereto (e.g. diabetic complications) comprising the combined administration of long-acting insulin (such as e.g. insulin glargine or insulin detemir) and a certain DPP-4 inhibitor, to pharmaceutical compositions and combinations comprising such active components, and to certain therapeutic uses thereof.

Further, the present invention relates to a method for improving glycemic control and/or preventing, reducing the risk of, slowing the progression of, delaying the onset or treating of complications of diabetes mellitus, such as micro- and macrovascular diseases (e.g. diabetic nephropathy, retinopathy or neuropathy, or cerebro- or cardiovascular complications such as e.g. myocardial infarction, stroke or vascular death or hospitalization), in a patient in need thereof (type 1 diabetes, LADA or, particularly, type 2 diabetes patient) comprising the combined (e.g. separate, simultaneous or sequential) administration of a long-acting insulin (such as e.g. insulin glargine or insulin detemir) and a certain DPP-4 inhibitor. Moreover, the present invention relates to a certain DPP-4 inhibitor for subcutaneous or transdermal (systemic) therapeutic use, particularly in treating and/or preventing the metabolic diseases described herein.

Furthermore, the present invention relates to a certain DPP-4 inhibitor for subcutaneous administration (particularly for subcutaneous injection), e.g. once daily, each other day, thrice weekly, twice weekly or once weekly, preferably less than once daily.

Furthermore, the present invention relates to a certain DPP-4 inhibitor for transdermal administration, e.g. once daily, each other day, thrice weekly, twice weekly or once weekly, preferably less than once daily.

Further, the present invention relates to a parenteral (preferably subcutaneous) delivery device, preferably a subcutaneous injection device, which may be with or without needle (e.g. a needle-based pen injector or a jet/needle-free injector), containing long-acting insulin and a certain DPP-4 inhibitor and, optionally, one or more pharmaceutically acceptable carriers and/or diluents.

Further, the present invention relates to a transdermal delivery device (e.g., a transdermal patch or gel) containing long-acting insulin and a certain DPP-4 inhibitor and, optionally, one or more pharmaceutically acceptable carriers and/or diluents.

Further, the present invention relates to the DPP-4 inhibitors and/or long-acting insulin, each as defined herein, for use in the combination therapies as described herein.

BRIEF DESCRIPTION OF THE DRAWINGS

FIG. 1 shows linagliptin activity in plasma after linagliptin subcutaneous (s.c.) dosing.

DETAILED DESCRIPTION OF THE INVENTION

The enzyme DPP-4 (dipeptidyl peptidase IV) also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

For example, DPP-4 inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769, WO2007/014886; WO 2004/050658, WO 2004/111051, WO 2005/058901, WO 2005/097798; WO 2006/068163, WO 2007/071738, WO 2008/017670; WO 2007/128721, WO 2007/128724, WO 2007/128761, or WO 2009/121945.

Long-acting insulin within the meaning of this invention refers to a formulation of insulin or insulin analogue that usually starts working within about 1-6 hours and is usually effective for up to 24 hours or more (e.g. up to 36 hours). Long-acting insulin usually provides a continuous level of insulin activity (for up to 24-36 hours) and usually operates at a maximum strength (with flat action profile) after about 8-12 hours, sometimes longer. Long-acting insulin is usually administered in the morning or before bed. Examples of long-acting insulin may include, but are not limited to, insulin glargine, insulin detemir or insulin degludec, which are insulin analogues, and ultralente insulin, which is regular human insulin formulated for slow absorption. Long-acting insulin is suited to provide for basal, as opposed to prandial, insulin requirements (e.g. to control hyperglycemia). Long-acting insulin may be typically administered ranging from twice or once daily, over thrice weekly up to once weekly (ultra longacting insulin). The route of administration of insulin may include, without being limited, invasive delivery (such as e.g. via parenteral route, preferentially via subcutaneous injection) or non-invasive delivery (such as e.g. via oral, buccal/sublingual, pulmonary, intranasal or transdermal (e.g. via iontophoresis, sonophoresis or vesicular carriers) route), with subcutaneously injectable long-acting insulin being preferred.

In one embodiment, the long-acting insulin of this invention refers to any basal insulin known in the art, preferably having a basal release profile. A basal release profile refers to the kinetic, amount and rate of release of the insulin or insulin analogue from the formulation into a patient's systemic circulation. In a graph of the patient's mean plasma insulin levels over time, a basal release profile typically has a minimal peak (often referred to as "a peakless profile" or "flat profile") and slowly and continuously releases insulin for a prolonged period of time.

In a further embodiment, the long-acting insulin is an acylated derivative of human insulin. Acylated insulin derivatives may be such wherein a lipophilic group is attached to the lysine residue in position B29. A commercial product is Levemir® comprising $Lys^{B29}(N^{\epsilon}$-tetradecanoyl) des(B30) human insulin (cf. insulin detemir). Another example is $N^{\epsilon B29}$-($N^{\alpha}$-(ω-carboxypentadecanoyl)-L-γ-glutamyl) des(B30) human insulin (cf. insulin degludec).

In a further embodiment, the long-acting insulin is such comprising positively charged amino acids such as Arg attached to the C-terminal end of the B-chain. A commercial product is Lantus® comprising $Gly^{A21}$, $Arg^{B31}$, $Arg^{B32}$ human insulin (cf. insulin glargine).

Insulin glargine (marketed as LANTUS® by Sanofi-Aventis) is approved and marketed for subcutaneous administration once a day. Insulin glargine provides relatively constant glucose lowering activity over a 24-hour period and may be administered any time during the day provided it is administered at the same time every day.

Insulin detemir (marketed as LEVEMIR® by Novo Nordisk) is approved and marketed for subcutaneous administration either twice a day or once a day, preferably with the evening meal or at bedtime.

Insulin degludec (NN1250) is a neutral, soluble ultra-long acting insulin with a duration of action more than 24 hours. Degludec has a very flat, predictable and smooth action profile. It is intended for subcutaneous administration once daily or less (e.g. three times a week).

In addition, further examples of long-acting insulin may include, without being limited to,
insulin lispro PEGylated with high molecular weight poly (ethylene glycol) derivatives especially as disclosed in WO 2009/152128 (the disclosure of which is incorporated herein), such as e.g. the PEGylated insulin lispro compound of the formula P-[(A)-(B)], or a pharmaceutically acceptable salt thereof, wherein A is the A-chain of insulin lispro, B is the B-chain of insulin lispro, and P is a PEG having a molecular weight in the range from about 17.5 kDa to about 40 kDa, and wherein A and B are properly cross-linked and P is attached via a urethane covalent bond to the epsilon-amino group of the lysine at position 28 of B;

amidated insulin glargine especially in the form of $Gly^{A21}$, $Arg^{B31}$, $Arg^{B32}$-$NH_2$ human insulin (insulin glargine amide, i.e. the C-terminus of the B-chain of insulin glargine is amidated) as disclosed in WO 2008/006496 or WO 2008/006496 (the disclosures of which are incorporated herein);

$Lys^{B29}(N^\epsilon$-lithocholyl-γ-Glu) des(B30) human insulin or $N^{\epsilon B29}$-ω-carboxypentadecanoyl-γ-amino-butanoyl des(B30) human insulin; or amidated insulin analogs as disclosed in WO 2009/087082 (the disclosure of which is incorporated herein), especially one selected from claim 14, or in WO 2009/087081 (the disclosure of which is incorporated herein), especially one selected from claim 16.

Long-acting insulin analogues are typically given as basic anti-diabetic therapy to type 2 diabetes, type 1 diabetes or latent autoimmune diabetes with onset in adults (LADA) patients to control the blood sugar when no food intake occurs. As mentioned above, this type of insulin provides a continuous level of insulin activity for up to 36 hours. Long-acting insulin operates at maximum strength after about 8-12 hours. Because of their advantages, it is thought that treatment with these insulin analogues can lead to a beneficial effect, for example less hypoglycaemia, less weight gain or a better metabolic control possibly resulting in less late diabetic complications such as problems with eyes, kidneys or feet and myocardial infarction, stroke or death. DPP-4 inhibitors are a diverse group of anti-diabetics, however also working via insulin increasing mechanisms and limited on still functioning B-cells for triggering endogenous insulin secretion. DPP-4 inhibitors lower glucagon levels and reduce post-prandial glucose peaks during food intake via increase of GLP-1 and subsequent mechanisms. The combination of this two principles is thereof a favorable approach in controlling efficacious fasted and post-prandial glucose levels. Also, by the complementary modes of action improved glucose tolerance, improved metabolic (glycemic) status and/or sustainable efficacy can be achieved and/or maintained over longer time. Linagliptin is the only DPP-4 inhibitor which demonstrates a superior pharmacokinetic profile (e.g. half life up to 72 h, stoichiometric reversible binding to DPP-4 protein) to be potentially administered once daily, each other day or even longer. In addition, various DPP-4 substrates (e.g. SDF-1, BNP) have been shown to have increased half lives and actions following inhibition of DPP-4 and thus being potentially of additional benefit for cardio-vascular outcome. The combination of linagliptin with insulin according to this invention thus is regarded to further decrease late stage macrovascular complications.

In the monitoring of the treatment of diabetes mellitus the HbA1c value, the product of a non-enzymatic glycation of the haemoglobin B chain, is of exceptional importance. As its formation depends essentially on the blood sugar level and the life time of the erythrocytes the HbA1c in the sense of a "blood sugar memory" reflects the average blood sugar level of the preceding 4-12 weeks. Diabetic patients whose HbA1c level has been well controlled over a long time by more intensive diabetes treatment (i.e. <6.5% of the total haemoglobin in the sample) are significantly better protected from diabetic microangiopathy. The available treatments for diabetes can give the diabetic an average improvement in their HbA1c level of the order of 1.0-1.5%. This reduction in the HbA1C level is not sufficient in all diabetics to bring them into the desired target range of <7.0%, preferably <6.5% and more preferably <6% HbA1c.

Within the meaning of this invention, inadequate or insufficient glycemic control means in particular a condition wherein patients show HbA1c values above 6.5%, in particular above 7.0%, even more preferably above 7.5%, especially above 8%. An embodiment of patients with inadequate or insufficient glycemic control include, without being limited to, patients having an HbA1c value from 7.5 to 10% (or, in another embodiment, from 7.5 to 11%). A special sub-embodiment of inadequately controlled patients refers to patients with poor glycemic control including, without being limited, patients having an HbA1c value ≥9%.

Within glycemic control, in addition to improvement of the HbA1c level, other recommended therapeutic goals for type 2 diabetes mellitus patients are improvement of fasting plasma glucose (FPG) and of postprandial plasma glucose (PPG) levels to normal or as near normal as possible. Recommended desired target ranges of preprandial (fasting) plasma glucose are 70-130 mg/dL (or 90-130 mg/dL) or <110 mg/dL, and of two-hour postprandial plasma glucose are <180 mg/dL or <140 mg/dL.

In one embodiment, diabetes patients within the meaning of this invention may include patients who have not previously been treated with an antidiabetic drug (drug-naïve patients). Thus, in an embodiment, the therapies described herein may be used in naïve patients. In another embodiment, diabetes patients within the meaning of this invention may include patients with advanced or late stage type 2 diabetes mellitus (including patients with failure to conventional antidiabetic therapy), such as e.g. patients with inadequate glycemic control on one, two or more conventional oral and/or non-oral antidiabetic drugs as defined herein, such as e.g. patients with insufficient glycemic control despite (mono-) therapy with metformin, a thiazolidinedione (particularly pioglitazone), a sulphonylurea, a glinide, GLP-1 or GLP-1 analogue, insulin or insulin analogue, or an α-glucosidase inhibitor, or despite dual combination therapy with metformin/sulphonylurea, metformin/thiazolidinedione (particularly pioglitazone), sulphonylurea/α-glucosidase inhibitor, pioglitazone/sulphonylurea, metformin/insulin, pioglitazone/insulin or sulphonylurea/insulin. Thus, in an embodiment, the therapies described herein may be used in patients experienced with therapy, e.g. with conventional oral and/or non-oral antidiabetic mono- or dual or triple combination medication as mentioned herein.

A further embodiment of diabetic patients within the meaning of this invention refers to patients ineligible for metformin therapy including
  patients for whom metformin therapy is contraindicated, e.g. patients having one or more contraindications against metformin therapy according to label, such as for example patients with at least one contraindication selected from:
    renal disease, renal impairment or renal dysfunction (e.g., as specified by product information of locally approved metformin),
    dehydration,
    unstable or acute congestive heart failure,
    acute or chronic metabolic acidosis, and
    hereditary galactose intolerance;
and
  patients who suffer from one or more intolerable side effects attributed to metformin, particularly gastrointestinal side effects associated with metformin, such as for example patients suffering from at least one gastrointestinal side effect selected from:
nausea,
vomiting,
diarrhea,
intestinal gas, and
severe abdominal discomfort.

A further embodiment of the diabetes patients which may be amenable to the therapies of this invention may include, without being limited, those diabetes patients for whom normal metformin therapy is not appropriate, such as e.g. those diabetes patients who need reduced dose metformin therapy due to reduced tolerability, intolerability or contraindication against metformin or due to (mildly) impaired/reduced renal function (including elderly patients, such as e.g. ≥60-65 years).

A further embodiment of diabetic patients within the meaning of this invention refers to patients having renal disease, renal dysfunction, or insufficiency or impairment of renal function (including mild, moderate and severe renal impairment), e.g. as suggested by elevated serum creatinine levels (e.g. serum creatinine levels above the upper limit of normal for their age, e.g. ≥130-150 μmol/l, or ≥1.5 mg/dl (≥136 μmol/l) in men and ≥1.4 mg/dl (≥124 μmol/l) in women) or abnormal creatinine clearance (e.g. glomerular filtration rate (GFR)≤30-60 ml/min).

In this context, for more detailed example, mild renal impairment may be e.g. suggested by a creatinine clearance of 50-80 ml/min (approximately corresponding to serum creatine levels of ≤1.7 mg/dL in men and ≤1.5 mg/dL in women); moderate renal impairment may be e.g. suggested by a creatinine clearance of 30-50 ml/min (approximately corresponding to serum creatinine levels of >1.7 to ≤3.0 mg/dL in men and >1.5 to ≤2.5 mg/dL in women); and severe renal impairment may be e.g. suggested by a creatinine clearance of <30 ml/min (approximately corresponding to serum creatinine levels of >3.0 mg/dL in men and >2.5 mg/dL in women). Patients with end-stage renal disease require dialysis (e.g. hemodialysis or peritoneal dialysis).

For other more detailed example, patients with renal disease, renal dysfunction or renal impairment include patients with chronic renal insufficiency or impairment, which can be stratified according to glomerular filtration rate (GFR, ml/min/1.73 m$^2$) into 5 disease stages: stage 1 characterized by normal GFR≥90 plus either persistent albuminuria or known structural or hereditary renal disease; stage 2 characterized by mild reduction of GFR (GFR 60-89) describing mild renal impairment; stage 3 characterized by moderate reduction of GFR (GFR 30-59) describing moderate renal impairment; stage 4 characterized by severe reduction of GFR (GFR 15-29) describing severe renal impairment; and terminal stage 5 characterized by requiring dialysis or GFR <15 describing established kidney failure (end-stage renal disease, ESRD).

A further embodiment of diabetic patients within the meaning of this invention refers to type 2 diabetes patients with or at risk of developing renal complications, such as diabetic nephropathy (including chronic and progressive renal insufficiency, albuminuria, proteinuria, fluid retention in the body (edema) and/or hypertension).

In a further embodiment, patients within the present invention may include type 1 diabetes, LADA or, particularly, type 2 diabetes patients, with or without obesity or overweight.

Within the scope of the present invention it has now been found that certain DPP-4 inhibitors as defined herein as well as pharmaceutical combinations, compositions or combined uses according to this invention of these DPP-4 inhibitors and long-acting insulin (such as e.g. insulin glargine, insulin detemir or insulin degludec) as defined herein have properties, which make them suitable for the purpose of this invention and/or for fulfilling one or more of above needs.

The present invention thus relates to a combination comprising a certain DPP-4 inhibitor (particularly BI 1356) and a long-acting insulin (such as e.g. insulin glargine, insulin detemir or insulin degludec), each as defined herein, particularly for simultaneous, separate or sequential use in the therapies described herein.

The present invention further relates to a certain DPP-4 inhibitor (particularly BI 1356) in combination with a long-acting insulin (such as e.g. insulin glargine, insulin detemir or insulin degludec), each as defined herein, for use in the therapies described herein.

The present invention further relates to a method for treating and/or preventing metabolic diseases, especially type 2 diabetes mellitus and/or conditions related thereto (e.g. diabetic complications) comprising the combined (e.g. simultaneous, separate or sequential) administration of an effective amount of a long-acting insulin (such as e.g. such as e.g. insulin glargine, insulin detemir or insulin degludec) as defined herein and of an effective amount of a DPP-4 inhibitor as defined herein to the patient (particularly human patient) in need thereof, such as e.g. a patient as described herein.

The present invention further relates to at least one of the following methods:
preventing, slowing the progression of, delaying or treating a metabolic disorder or disease, such as e.g. type 1 diabetes mellitus, type 2 diabetes mellitus, impaired glucose tolerance (IGT), impaired fasting blood glucose (IFG), hyperglycemia, postprandial hyperglycemia, postabsorptive hyperglycemia, overweight, obesity, dyslipidemia, hyperlipidemia, hypercholesterolemia, hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome;
improving and/or maintaining glycemic control and/or for reducing of fasting plasma glucose, of postprandial plasma glucose, of postabsorptive plasma glucose and/or of glycosylated hemoglobin HbA1c;
preventing, slowing, delaying or reversing progression from pre-diabetes, impaired glucose tolerance (IGT), impaired fasting blood glucose (IFG), insulin resistance and/or from metabolic syndrome to type 2 diabetes mellitus;
preventing, reducing the risk of, slowing the progression of, delaying or treating of complications of diabetes mellitus such as micro- and macrovascular diseases, such as nephropathy, micro- or macroalbuminuria, proteinuria, retinopathy, cataracts, neuropathy, learning or memory impairment, neurodegenerative or cognitive disorders, cardio- or cerebrovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy, heart failure, heart rhythm disorders, vascular restenosis, and/or stroke;
reducing body weight and/or body fat and/or liver fat and/or intra-myocellular fat or preventing an increase in body weight and/or body fat and/or liver fat and/or intra-myocellular fat or facilitating a reduction in body weight and/or body fat and/or liver fat and/or intra-myocellular fat;

preventing, slowing, delaying or treating the degeneration of pancreatic beta cells and/or the decline of the functionality of pancreatic beta cells and/or for improving, preserving and/or restoring the functionality of pancreatic beta cells and/or stimulating and/or restoring or protecting the functionality of pancreatic insulin secretion;

preventing, slowing, delaying or treating non alcoholic fatty liver disease (NAFLD) including hepatic steatosis, non-alcoholic steatohepatitis (NASH) and/or liver fibrosis (such as e.g. preventing, slowing the progression, delaying, attenuating, treating or reversing hepatic steatosis, (hepatic) inflammation and/or an abnormal accumulation of liver fat);

preventing, slowing the progression of, delaying or treating type 2 diabetes with failure to conventional antidiabetic mono- or combination therapy;

achieving a reduction in the dose of conventional antidiabetic medication required for adequate therapeutic effect;

reducing the risk for adverse effects associated with conventional antidiabetic medication (e.g. hypoglycemia or weight gain); and/or maintaining and/or improving the insulin sensitivity and/or for treating or preventing hyperinsulinemia and/or insulin resistance;

in a patient in need thereof (such as e.g. a patient as described herein), said method comprising combined (e.g. simultaneous, separate or sequential) administration of a DPP-4 inhibitor as defined herein and a long-acting insulin as defined herein.

The present invention further relates to a certain DPP-4 inhibitor (particularly BI 1356) as defined herein for subcutaneous or transdermal use in the therapies described herein.

The present invention further relates to a method for treating and/or preventing metabolic diseases, especially type 2 diabetes mellitus and/or conditions related thereto (e.g. diabetic complications) comprising the administration of an effective amount of a DPP-4 inhibitor as defined herein, optionally in combination with one or more other therapeutic agents as described herein, to the patient (particularly human patient) in need thereof (such as e.g. a patient as described herein), wherein the administration of the DPP-4 inhibitor, and of optionally one or more other therapeutic agents, is by parenteral, such as e.g. subcutaneous or transdermal route.

The present invention further relates to the use of a DPP-4 inhibitor as defined herein for the manufacture of a pharmaceutical composition for subcutaneous use in the treatment and/or prevention of a metabolic disease, disorder or condition such as e.g. described herein, especially type 2 diabetes mellitus and/or conditions related thereto (e.g. diabetic complications).

The present invention further relates to at least one of the following methods:

preventing, slowing the progression of, delaying or treating a metabolic disorder or disease, such as e.g. type 1 diabetes mellitus, type 2 diabetes mellitus, impaired glucose tolerance (IGT), impaired fasting blood glucose (IFG), hyperglycemia, postprandial hyperglycemia, postabsorptive hyperglycemia, overweight, obesity, dyslipidemia, hyperlipidemia, hypercholesterolemia, hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome;

improving and/or maintaining glycemic control and/or for reducing of fasting plasma glucose, of postprandial plasma glucose, of postabsorptive plasma glucose and/or of glycosylated hemoglobin HbA1c;

preventing, slowing, delaying or reversing progression from pre-diabetes, impaired glucose tolerance (IGT), impaired fasting blood glucose (IFG), insulin resistance and/or from metabolic syndrome to type 2 diabetes mellitus;

preventing, reducing the risk of, slowing the progression of, delaying or treating of complications of diabetes mellitus such as micro- and macrovascular diseases, such as nephropathy, micro- or macroalbuminuria, proteinuria, retinopathy, cataracts, neuropathy, learning or memory impairment, neurodegenerative or cognitive disorders, cardio- or cerebrovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy, heart failure, heart rhythm disorders, vascular restenosis, and/or stroke;

reducing body weight and/or body fat and/or liver fat and/or intra-myocellular fat or preventing an increase in body weight and/or body fat and/or liver fat and/or intra-myocellular fat or facilitating a reduction in body weight and/or body fat and/or liver fat and/or intra-myocellular fat;

preventing, slowing, delaying or treating the degeneration of pancreatic beta cells and/or the decline of the functionality of pancreatic beta cells and/or for improving, preserving and/or restoring the functionality of pancreatic beta cells and/or stimulating and/or restoring or protecting the functionality of pancreatic insulin secretion;

preventing, slowing, delaying or treating non alcoholic fatty liver disease (NAFLD) including hepatic steatosis, non-alcoholic steatohepatitis (NASH) and/or liver fibrosis (such as e.g. preventing, slowing the progression, delaying, attenuating, treating or reversing hepatic steatosis, (hepatic) inflammation and/or an abnormal accumulation of liver fat);

preventing, slowing the progression of, delaying or treating type 2 diabetes with failure to conventional antidiabetic mono- or combination therapy;

achieving a reduction in the dose of conventional antidiabetic medication required for adequate therapeutic effect;

reducing the risk for adverse effects associated with conventional antidiabetic medication (e.g. hypoglycemia or weight gain); and/or maintaining and/or improving the insulin sensitivity and/or for treating or preventing hyperinsulinemia and/or insulin resistance;

in a patient in need thereof (such as e.g. a patient as described herein), said method comprising the parenteral, preferably subcutaneous or transdermal, administration of a DPP-4 inhibitor as defined herein, optionally in combination with one or more other therapeutic agents as described herein.

Further, the present invention relates to the combination according to this invention comprising a DPP-4 inhibitor as defined herein and a long-acting insulin as defined herein for parenteral, particularly subcutaneous or transdermal, administration of one or both of the active components to the patient in need thereof.

Further, the present invention relates to a pharmaceutical composition according to this invention comprising
a DPP-4 inhibitor as defined herein,
a long-acting insulin as defined herein,
and, optionally, one or more pharmaceutically acceptable carriers and/or diluents, said composition being for subcutaneous administration to the patient in need thereof, e.g. by injection.

In addition, the present invention relates to the combination according to this invention comprising a DPP-4 inhibitor as defined herein and a long-acting insulin as defined herein for use in treating and/or preventing (including slowing the progression or delaying the onset) of metabolic diseases as defined herein, particularly diabetes (especially type 2 diabetes or conditions related thereto, including diabetic complications), optionally in combination with one or more other therapeutic agents as described herein.

In addition, the present invention relates to the use of a combination according to this invention comprising a DPP-4 inhibitor as defined herein and a long-acting insulin as defined herein for the manufacture of a medicament for use in a therapeutic method as described hereinbefore or hereinafter.

In addition, the present invention relates to a combination according to this invention comprising a DPP-4 inhibitor as defined herein and a long-acting insulin as defined herein for use in a therapeutic method as described hereinbefore or hereinafter.

In addition, the present invention relates to a method of treating and/or preventing (including slowing the progression or delaying the onset) of a metabolic disease, particularly diabetes (especially type 2 diabetes) or conditions related thereto, including diabetic complications, comprising administering to the patient in need thereof (such as e.g. a patient as described herein) a combination according to this invention comprising a DPP-4 inhibitor as defined herein and a long-acting insulin as defined herein.

In addition, the present invention relates a DPP-4 inhibitor as defined herein for use in a method as described hereinbefore or hereinafter, said method comprising administering the DPP-4 inhibitor, optionally combined with one or more other active substances (e.g. which may selected from those mentioned herein, such as e.g. metformin or pioglitazone), in combination (e.g. separately, simultaneously or sequentially) with a long-acting insulin as defined herein to the patient In addition, the present invention relates a long-acting insulin as defined herein for use in a method as described hereinbefore or hereinafter, said method comprising administering the long-acting insulin, optionally combined with one or more other active substances (e.g. which may selected from those mentioned herein, such as e.g. metformin or pioglitazone), in combination (e.g. separately, simultaneously or sequentially) with a DPP-4 inhibitor as defined herein to the patient In addition, the present invention relates to the use of a DPP-4 inhibitor as defined herein for the manufacture of a medicament for use in combination with a long-acting insulin as defined herein for treating and/or preventing (including slowing the progression or delaying the onset) of metabolic diseases, particularly diabetes (especially type 2 diabetes) and conditions related thereto, including diabetic complications.

In addition, the present invention relates to the use of a long-acting insulin as defined herein for the manufacture of a medicament for use in combination with a DPP-4 inhibitor as defined herein for treating and/or preventing (including slowing the progression or delaying the onset) of metabolic diseases, particularly diabetes (especially type 2 diabetes) or conditions related thereto, including diabetic complications.

In addition, the present invention relates to the use of a DPP-4 inhibitor as defined herein, optionally in combination with one or more other active substances (such as e.g. metformin or pioglitazone), for the manufacture of a medicament for use in combination with a long-acting insulin as defined herein for treating and/or preventing (including slowing the progression or delaying the onset) of metabolic diseases, particularly diabetes (especially type 2 diabetes) or conditions related thereto, including diabetic complications.

In addition, the present invention relates a DPP-4 inhibitor as defined herein for use in a combination treatment according to the invention in a patient in need thereof (such as e.g. a patient as described herein).

In addition, the present invention relates a long-acting insulin as defined herein for use in a combination treatment according to the invention in a patient in need thereof (such as e.g. a patient as described herein).

In addition, the present invention relates a DPP-4 inhibitor as defined herein, optionally in combination with one or more other active substances (such as e.g. metformin or pioglitazone), for use in a combination treatment according to the invention in a patient in need thereof.

In addition, the invention relates to a DPP-4 inhibitor as defined herein for use in a method as described hereinbefore or hereinafter, said method comprising administering the DPP-4 inhibitor, optionally in combination with one or more other active substances (e.g. which may selected from those mentioned herein, such as e.g. metformin or pioglitazone), to the patient.

Further, the invention relates to a DPP-4 inhibitor as defined herein for use in a method of preventing, reducing the risk of, slowing the progression of, delaying or treating weight gain associated with the therapy with a long-acting insulin as defined herein, preferably said method comprising administering the DPP-4 inhibitor and the long-acting insulin to the patient (e.g. type 1 diabetes, LADA or, particularly, type 2 diabetes patient, with or without obesity or overweight).

Further, the invention relates to a DPP-4 inhibitor as defined herein for use in a method of preventing, reducing the risk of, slowing the progression of, delaying or treating an increase in body weight and/or body fat and/or liver fat and/or intra-myocellular fat which may be associated with the therapy with a long-acting insulin as defined herein, preferably said method comprising administering the DPP-4 inhibitor and the long-acting insulin to the patient (e.g. type 1 diabetes, LADA or, particularly, type 2 diabetes patient, with or without obesity or overweight).

Further, the invention relates to a DPP-4 inhibitor as defined herein for use in a method of improving body fat composition and/or obesity parameters which may be associated with the therapy with a long-acting insulin as defined herein, preferably said method comprising administering the DPP-4 inhibitor and the long-acting insulin to the patient (e.g. type 1 diabetes, LADA or, particularly, type 2 diabetes patient, with or without obesity or overweight).

Further, the invention relates to a DPP-4 inhibitor and a long-acting insulin each as defined herein for use in a method of improving diabetic phenotype, improving glycemic and/or metabolic control, improving (blood) glucose profile (e.g. improving the control of fasting and/or postprandial blood glucose levels) and/or improving glucagon suppression (e.g. over long-term and/or during chronic treatment), preferably said method comprising administering the DPP-4 inhibitor and the long-acting insulin to the patient (e.g. type 1 diabetes, LADA or, particularly, type 2 diabetes patient, with or without obesity or overweight).

Further, the invention relates to a DPP-4 inhibitor as defined herein for use in a method of sparing or reducing the amount of long-acting insulin as defined herein required for efficacious and/or safe therapeutic treatment, said method comprising administering the DPP-4 inhibitor and the long-acting insulin to the patient (e.g. type 1 diabetes, LADA or, particularly, type 2 diabetes patient, with or without obesity or overweight).

Further, the invention relates to a DPP-4 inhibitor as defined herein for use in a therapeutic or preventive method as described herein, said use comprising adding the DPP-4 inhibitor to long-acting insulin as defined herein alone or in combination with one or more other antidiabetic drugs (e.g. selected from metformin, pioglitazone and a sulphonylurea), e.g. for improving glycemic control in a patient (e.g. type 1 diabetes, LADA or, particularly, type 2 diabetes patient, with or without obesity or overweight) who may be inadequately controlled on insulin alone or in combination with one or more other antidiabetic drugs (e.g. selected from metformin, pioglitazone and a sulphonylurea).

Further, the invention relates to a DPP-4 inhibitor and a long-acting insulin each as defined herein for use in a therapeutic or preventive method as described herein, said use comprising adding the DPP-4 inhibitor and the long-acting insulin to one or more other antidiabetic drugs (e.g. selected from metformin, pioglitazone and a sulphonylurea), e.g. for improving glycemic control in a patient (e.g. type 1 diabetes, LADA or, particularly, type 2 diabetes patient, with or without obesity or overweight) who may be inadequately controlled on one or more other antidiabetic drugs (e.g. selected from metformin, pioglitazone and a sulphonylurea).

Further, the invention relates to a long-acting insulin as defined herein for use in a therapeutic or preventive method as described herein, said use comprising adding the long-acting insulin to a DPP-4 inhibitor as defined herein alone or in combination with one or more other antidiabetic drugs (e.g. selected from metformin, pioglitazone and a sulphonylurea), e.g. for improving glycemic control in a patient (e.g. type 1 diabetes, LADA or, particularly, type 2 diabetes patient, with or without obesity or overweight) who may be inadequately controlled on a DPP-4 inhibitor alone or in combination with one or more other antidiabetic drugs (e.g. selected from metformin, pioglitazone and a sulphonylurea).

Further, the invention relates to a combination or composition comprising a DPP-4 inhibitor and a long-acting insulin each as defined herein for use in treatment and/or prevention as described herein, optionally in combination with one or more other therapeutic agents.

Further, the invention relates to a DPP-4 inhibitor as defined herein with or without metformin and/or pioglitazone in combination with a long-acting insulin as defined herein for therapeutic or preventive use as described herein.

Further, the invention relates to a DPP-4 inhibitor as defined herein in combination with a long-acting insulin as defined herein, with or without metformin, for use in a method of therapy or prophylaxis as described herein.

Other aspects of the present invention become apparent to the skilled person from the foregoing and following remarks (including the examples and claims).

The aspects of the present invention, in particular the pharmaceutical compounds, compositions, combinations, methods and uses, refer to DPP-4 inhibitors and/or long-acting insulins as defined hereinbefore and hereinafter.

A DPP-4 inhibitor within the meaning of the present invention includes, without being limited to, any of those DPP-4 inhibitors mentioned hereinabove and hereinbelow, preferably orally and/or subcutaneously active DPP-4 inhibitors.

An embodiment of this invention refers to a DPP-4 inhibitor for use in the treatment and/or prevention of metabolic diseases (particularly type 2 diabetes mellitus) in type 2 diabetes patients, wherein said patients further suffering from renal disease, renal dysfunction or renal impairment, particularly characterized in that said DPP-4 inhibitor is administered to said patients in the same dose levels as to patients with normal renal function, thus e.g. said DPP-4 inhibitor does not require downward dosing adjustment for impaired renal function.

For example, a DPP-4 inhibitor according to this invention (especially one which may be suited for patients with impaired renal function) may be such an oral DPP-4 inhibitor, which and whose active metabolites have preferably a relatively wide (e.g. about >100 fold) therapeutic window and/or, especially, that are primarily eliminated via hepatic metabolism or biliary excretion (preferably without adding additional burden to the kidney).

In more detailed example, a DPP-4 inhibitor according to this invention (especially one which may be suited for patients with impaired renal function) may be such an orally administered DPP-4 inhibitor, which has a relatively wide (e.g. >100 fold) therapeutic window (preferably a safety profile comparable to placebo) and/or which fulfils one or more of the following pharmacokinetic properties (preferably at its therapeutic oral dose levels):

- The DPP-4 inhibitor is substantially or mainly excreted via the liver (e.g. >80% or even >90% of the administered oral dose), and/or for which renal excretion represents no substantial or only a minor elimination pathway (e.g. <10%, preferably <7%, of the administered oral dose measured, for example, by following elimination of a radiolabelled carbon ($^{14}C$) substance oral dose);
- The DPP-4 inhibitor is excreted mainly unchanged as parent drug (e.g. with a mean of >70%, or >80%, or, preferably, 90% of excreted radioactivity in urine and faeces after oral dosing of radiolabelled carbon ($^{14}C$) substance), and/or which is eliminated to a non-substantial or only to a minor extent via metabolism (e.g. <30%, or <20%, or, preferably, 10%);
- The (main) metabolite(s) of the DPP-4 inhibitor is/are pharmacologically inactive. Such as e.g. the main metabolite does not bind to the target enzyme DPP-4 and, optionally, it is rapidly eliminated compared to the parent compound (e.g. with a terminal half-life of the metabolite of ≤20 h, or, preferably, ≤about 16 h, such as e.g. 15.9 h).

In one embodiment, the (main) metabolite in plasma (which may be pharmacologically inactive) of a DPP-4 inhibitor having a 3-amino-piperidin-1-yl substituent is such a derivative where the amino group of the 3-amino-piperidin-1-yl moiety is replaced by a hydroxyl group to form the 3-hydroxy-piperidin-1-yl moiety (e.g. the 3-(S)-hydroxy-piperidin-1-yl moiety, which is formed by inversion of the configuration of the chiral center).

Further properties of a DPP-4 inhibitor according to this invention may be one or more of the following: Rapid attainment of steady state (e.g. reaching steady state plasma levels (>90% of the steady state plasma concentration) between second and fifth day of treatment with therapeutic oral dose levels), little accumulation (e.g. with a mean accumulation ratio $R_{A,AUC}$≤1.4 with therapeutic oral dose levels), and/or preserving a long-lasting effect on DPP-4 inhibition, preferably when used once-daily (e.g. with almost complete (>90%) DPP-4 inhibition at therapeutic oral dose levels, >80% inhibition over a 24 h interval after once-daily intake of therapeutic oral drug dose), significant decrease in 2 h postprandial blood glucose excursions by ≥80% (already on first day of therapy) at therapeutic dose levels, and cumulative amount of unchanged parent compound excreted in urine on first day being below 1% of the administered dose and increasing to not more than about 3-6% in steady state.

Thus, for example, a DPP-4 inhibitor according to this invention may be characterized in that said DPP-4 inhibitor has a primarily non-renal route of excretion, i.e. said DPP-4 inhibitor is excreted to a non-substantial or only to a minor extent (e.g. <10%, preferably <7%, e.g. about 5%, of administered oral dose, preferably of oral therapeutic dose) via the kidney (measured, for example, by following elimination of a radiolabelled carbon ($^{14}$C) substance oral dose).

Further, a DPP-4 inhibitor according to this invention may be characterized in that said DPP-4 inhibitor is excreted substantially or mainly via the liver or faeces (measured, for example, by following elimination of a radiolabelled carbon ($^{14}$C) substance oral dose).

Further, a DPP-4 inhibitor according to this invention may be characterized in that said DPP-4 inhibitor is excreted mainly unchanged as parent drug (e.g. with a mean of >70%, or >80%, or, preferably, 90% of excreted radioactivity in urine and faeces after oral dosing of radiolabelled carbon ($^{14}$C) substance), said DPP-4 inhibitor is eliminated to a non-substantial or only to a minor extent via metabolism, and/or the main metabolite of said DPP-4 inhibitor is pharmacologically inactive or has a relatively wide therapeutic window.

Further, a DPP-4 inhibitor according to this invention may be characterized in that said DPP-4 inhibitor does not significantly impair glomerular and/or tubular function of a type 2 diabetes patient with chronic renal insufficiency (e.g. mild, moderate or severe renal impairment or end stage renal disease), and/or said DPP-4 inhibitor trough levels in the blood plasma of type 2 diabetes patients with mild or moderate renal impairment are comparable to the levels in patients with normal renal function, and/or said DPP-4 inhibitor does not require to be dose-adjusted in a type 2 diabetes patient with impaired renal function (e.g. mild, moderate or severe renal impairment or end stage renal disease, preferably regardless of the stage of renal impairment).

Further, a DPP-4 inhibitor according to this invention may be characterized in that said DPP-4 inhibitor provides its minimally effective dose at that dose that results in >50% inhibition of DPP-4 activity at trough (24 h after last dose) in >80% of patients, and/or said DPP-4 inhibitor provides its fully therapeutic dose at that dose that results in >80% inhibition of DPP-4 activity at trough (24 h after last dose) in >80% of patients.

Further, a DPP-4 inhibitor according to this invention may be characterized in that being suitable for use in type 2 diabetes patients who are with diagnosed renal impairment and/or who are at risk of developing renal complications, e.g. patients with or at risk of diabetic nephropathy (including chronic and progressive renal insufficiency, albuminuria, proteinuria, fluid retention in the body (edema) and/or hypertension).

In a first embodiment (embodiment A), a DPP-4 inhibitor in the context of the present invention is any DPP-4 inhibitor of formula (I)

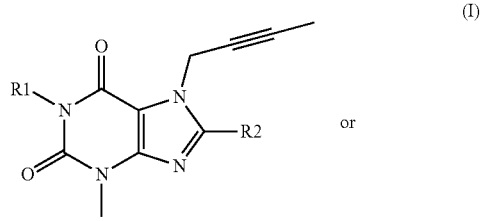

or formula (II)

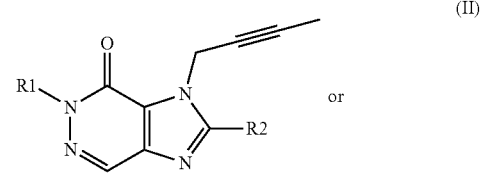

or formula (III)

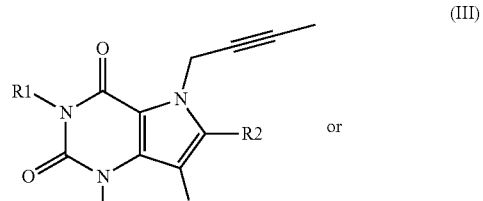

or formula (IV)

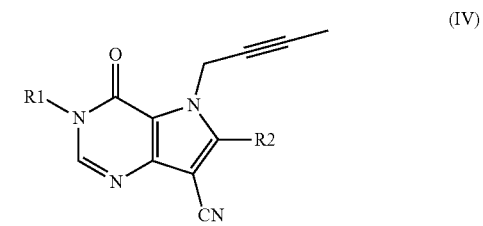

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl)methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino, or its pharmaceutically acceptable salt.

In a second embodiment (embodiment B), a DPP-4 inhibitor in the context of the present invention is a DPP-4 inhibitor selected from the group consisting of sitagliptin, vildagliptin, saxagliptin, alogliptin, gemigliptin, (2S)-1-{[2-(5-Methyl-2-phenyl-oxazol-4-yl)-ethylamino]-acetyl}-pyrrolidine-2-carbonitrile, (2S)-1-{[1,1,-Dimethyl-3-(4-pyridin-3-yl-imidazol-1-yl)-propyl amino]-acetyl}-pyrrolidine-2-carbonitrile, (S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one, (3,3-Difluoropyrrolidin-1-yl)-((2S,4S)-4-(4-(pyrimidin-2-yl)piperazin-1-yl)pyrrolidin-2-yl)methanone, (1((3S,4S)-4-amino-1-(4-(3,3-difluoropyrrolidin-1-yl)-1,3,5-triazin-2-yl)pyrrolidin-3-yl)-5,5-difluoropiperidin-2-one, (2S,4S)-1-{2-[(3S,1R)-3-(1H-1,2,4-Triazol-1-ylmethyl)cyclopentylamino]-acetyl}-4-fluoropyrrolidine-2-carbonitrile, (R)-2-[6-(3-Amino-piperidin-1-yl)-3-methyl-2,4-dioxo-3,4-dihydro-2H-pyrimidin-1-ylmethyl]-4-fluoro-benzonitrile, 5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide, 3-{(2S,4S)-4-[4-(3-Methyl-1-phenyl-1H-pyrazol-5-yl)piperazin-1-yl]pyrrolidin-2-ylcarbonyl}thiazolidine,

[(2R)-1-{[(3R)-pyrrolidin-3-ylamino]acetyl}pyrrolidin-2-yl]boronic acid, (2S,4S)-1-[2-[(4-ethoxycarbonylbicyclo[2.2.2]oct-1-yl)amino]acetyl]-4-fluoropyrrolidine-2-carbonitrile, 2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile, 6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione, and (S)-2-methylpyrazolo[1,5-a]primidine-6-carboxylic acid {2-[(2-cyanopyrrolidin-1-yl)-2-oxoethylamino]-2-methylpropyl}amide, or its pharmaceutically acceptable salt.

Regarding the first embodiment (embodiment A), preferred DPP-4 inhibitors are any or all of the following compounds and their pharmaceutically acceptable salts:

1-[(4-methyl-quinazolin-2-yl)-methyl]-3-methyl-7-(2-butyn-1-yl)-8-(3-(R)-amino-piperidin-1-yl)-xanthine (compare WO 2004/018468, example 2(142)):

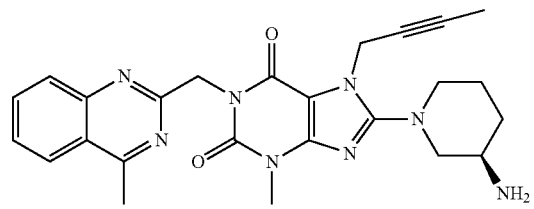 [SMILES: CC#CCn1c(N2CCC[C@@H](N)C2)nc2c1c(=O)n(Cc1nc(C)c3ccccc3n1)c(=O)n2C]

1-[([1,5]naphthyridin-2-yl)-methyl]-3-methyl-7-(2-butyn-1-yl)-8-((R)-3-amino-piperidin-1-yl)-xanthine (compare WO 2004/018468, example 2(252)):

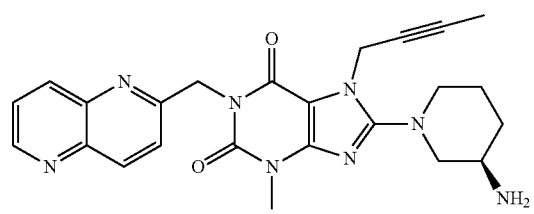

1-[(Quinazolin-2-yl)-methyl]-3-methyl-7-(2-butyn-1-yl)-8-((R)-3-amino-piperidin-1-yl)-xanthine (compare WO 2004/018468, example 2(80)):

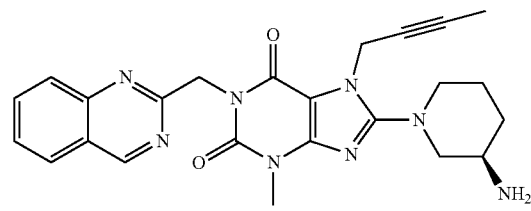 [SMILES: CC#CCn1c(N2CCC[C@@H](N)C2)nc2c1c(=O)n(Cc1ncc3ccccc3n1)c(=O)n2C]

2-((R)-3-Amino-piperidin-1-yl)-3-(but-2-yinyl)-5-(4-methyl-quinazolin-2-ylmethyl)-3,5-dihydro-imidazo[4,5-d]pyridazin-4-one (compare WO 2004/050658, example 136):

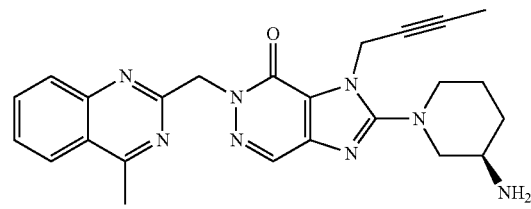 [SMILES: CC#CCn1c(N2CCC[C@@H](N)C2)nc2cnn(Cc3nc(C)c4ccccc4n3)c(=O)c21]

1-[(4-Methyl-quinazolin-2-yl)methyl]-3-methyl-7-(2-butyin-1-yl)-8-[(2-amino-2-methyl-propyl)-methylamino]-xanthine (compare WO 2006/029769, example 2(1)):

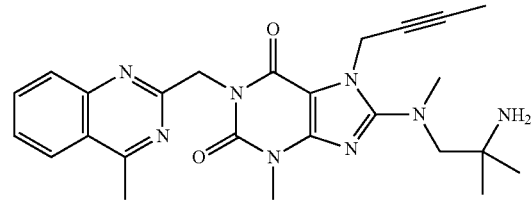 [SMILES: CC#CCn1c(N(C)CC(C)(C)N)nc2c1c(=O)n(Cc1nc(C)c3ccccc3n1)c(=O)n2C]

1-[(3-Cyano-quinolin-2-yl)methyl]-3-methyl-7-(2-butyn-1-yl)-8-(R)-3-amino-piperidin-1-yl)-xanthine (compare WO 2005/085246, example 1(30)):

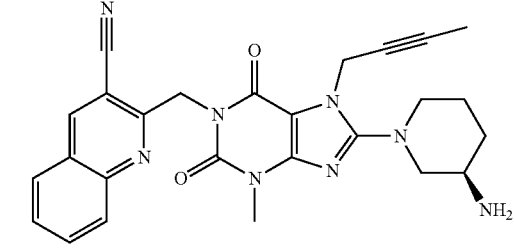 [SMILES: CC#CCn1c(N2CCC[C@@H](N)C2)nc2c1c(=O)n(Cc1nc3ccccc3cc1C#N)c(=O)n2C]

1-(2-Cyano-benzyl)-3-methyl-7-(2-butyn-1-yl)-8-((R)-3-amino-piperidin-1-yl)-xanthine (compare WO 2005/085246, example 1(39)):

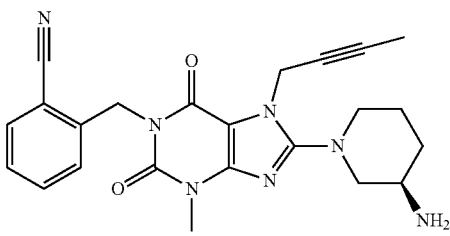 [SMILES: CC#CCn1c(N2CCC[C@@H](N)C2)nc2c1c(=O)n(Cc1ccccc1C#N)c(=O)n2C]

1-[(4-Methyl-quinazolin-2-yl)methyl]-3-methyl-7-(2-butyn-1-yl)-8-[(S)-(2-amino-propyl)-methylamino]-xanthine (compare WO 2006/029769, example 2(4)):

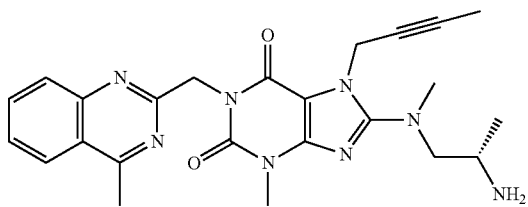 [SMILES: CC#CCn1c(N(C)C[C@H](C)N)nc2c1c(=O)n(Cc1nc(C)c3ccccc3n1)c(=O)n2C]

1-[(3-Cyano-pyridin-2-yl)methyl]-3-methyl-7-(2-butyn-1-yl)-8-((R)-3-amino-piperidin-1-yl)-xanthine (compare WO 2005/085246, example 1(52)):

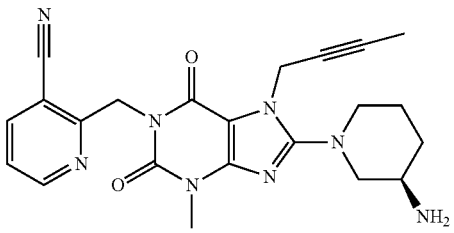 [SMILES: CC#CCn1c(N2CCC[C@@H](N)C2)nc2c1c(=O)n(Cc1ncccc1C#N)c(=O)n2C]

1-[(4-Methyl-pyrimidin-2-yl)methyl]-3-methyl-7-(2-butyn-1-yl)-8-(R)-3-amino-piperidin-1-yl)-xanthine (compare WO 2005/085246, example 1(81)):

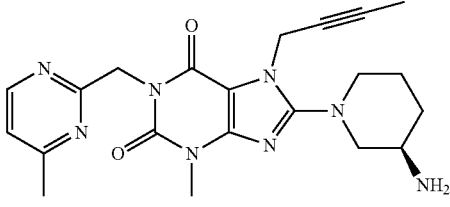 [SMILES: CC#CCn1c(N2CCC[C@@H](N)C2)nc2c1c(=O)n(Cc1nccc(C)n1)c(=O)n2C]

1-[(4,6-Dimethyl-pyrimidin-2-yl)methyl]-3-methyl-7-(2-butyn-1-yl)-8-(R)-3-amino-piperidin-1-yl)-xanthine (compare WO 2005/085246, example 1(82)):

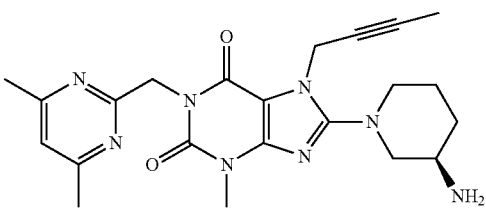 [SMILES: CC#CCn1c(N2CCC[C@@H](N)C2)nc2c1c(=O)n(Cc1nc(C)cc(C)n1)c(=O)n2C]

1-[(Quinoxalin-6-yl)methyl]-3-methyl-7-(2-butyn-1-yl)-8-((R)-3-amino-piperidin-1-yl)-xanthine (compare WO 2005/085246, example 1(83)):

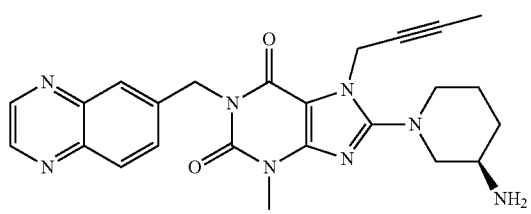 [SMILES: CC#CCn1c(N2CCC[C@@H](N)C2)nc2c1c(=O)n(Cc1ccc3nccnc3c1)c(=O)n2C]

These DPP-4 inhibitors are distinguished from structurally comparable DPP-4 inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

A more preferred DPP-4 inhibitor among the abovementioned DPP-4 inhibitors of embodiment A of this invention is 1-[(4-methyl-quinazolin-2-yl)methyl]-3-methyl-7-(2-butyn-1-yl)-8-(3-(R)-amino-piperidin-1-yl)-xanthine, particularly the free base thereof (which is also known as linagliptin or BI 1356).

As further DPP-4 inhibitors the following compounds can be mentioned:

Sitagliptin (MK-0431) having the structural formula A below is (3R)-3-amino-1-[3-(trifluoromethyl)-5,6,7,8-tetrahydro-5H-[1,2,4]triazolo[4,3-a]pyrazin-7-yl]-4-(2,4,5-trifluorophenyl)butan-1-one, also named (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine,

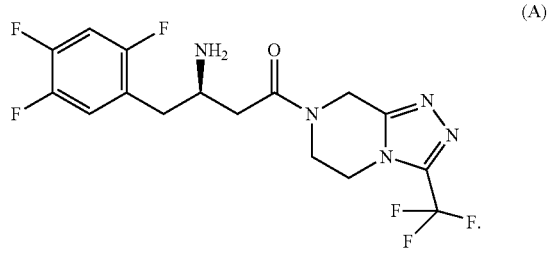 [SMILES: N[C@@H](CC(=O)N1CCn2c(nnc2C(F)(F)F)C1)Cc1cc(F)c(F)cc1F]

(A)

In one embodiment, sitagliptin is in the form of its dihydrogenphosphate salt, i.e. sitagliptin phosphate. In a further embodiment, sitagliptin phosphate is in the form of a crystalline anhydrate or monohydrate. A class of this embodiment refers to sitagliptin phosphate monohydrate. Sitagliptin free base and pharmaceutically acceptable salts thereof are disclosed in U.S. Pat. No. 6,699,871 and in Example 7 of WO 03/004498. Crystalline sitagliptin phosphate monohydrate is disclosed in WO 2005/003135 and in WO 2007/050485. For details, e.g. on a process to manufacture, to formulate or to use this compound or a salt thereof, reference is thus made to these documents.

A tablet formulation for sitagliptin is commercially available under the trade name Januvia®. A tablet formulation for sitagliptin/metformin combination is commercially available under the trade name Janumet®.

Vildagliptin (LAF-237) having the structural formula B below is (2S)-{[(3-hydroxyadamantan-1-yl)amino] acetyl}pyrrolidine-2-carbonitrile, also named (S)-1-[(3-hydroxy-1-adamantyl)amino]acetyl-2-cyano-pyrrolidine,

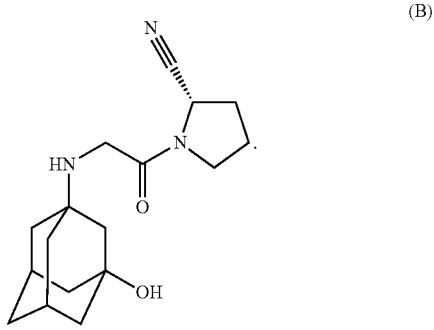 [SMILES: N#C[C@@H]1CCCN1C(=O)CNC12CC3CC(CC(O)(C3)C1)C2]

(B)

Vildagliptin is specifically disclosed in U.S. Pat. No. 6,166,063 and in Example 1 of WO 00/34241. Specific salts of vildagliptin are disclosed in WO 2007/019255. A crystalline form of vildagliptin as well as a vildagliptin tablet formulation are disclosed in WO 2006/078593. Vildagliptin can be formulated as described in WO 00/34241 or in WO 2005/067976. A modified release vildagliptin formulation is described in WO 2006/135723.

For details, e.g. on a process to manufacture, to formulate or to use this compound or a salt thereof, reference is thus made to these documents.

A tablet formulation for vildagliptin is expected to be commercially available under the trade name Galvus®. A tablet formulation for vildagliptin/metformin combination is commercially available under the trade name Eucreas®.

Saxagliptin (BMS-477118) having the structural formula C below is (1S,3S,5S)-2-{(2S)-2-amino-2-(3-hydroxy-adamantan-1-yl)acetyl}-2-azabicyclo[3.1.0]hexane-3-carbonitrile, also named (S)-3-hydroxyadamantylglycine-L-cis-4,5-methanoprolinenitrile,

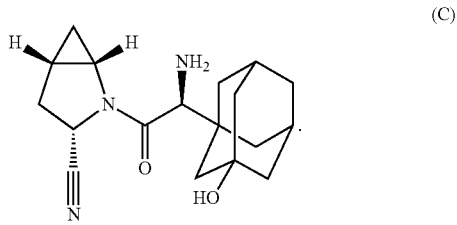 [SMILES: N#C[C@@H]1C[C@@H]2C[C@@H]2N1C(=O)[C@@H](N)C12CC3CC(CC(O)(C3)C1)C2]

(C)

Saxagliptin is specifically disclosed in U.S. Pat. No. 6,395,767 and in Example 60 of WO 01/68603.

In one embodiment, saxagliptin is in the form of its HCl salt or its mono-benzoate salt as disclosed in WO 2004/052850. In a further embodiment, saxagliptin is in the form of the free base. In a yet further embodiment, saxagliptin is in the form of the monohydrate of the free base as disclosed in WO 2004/052850. Crystalline forms of the HCl salt and of the free base of saxagliptin are disclosed in WO 2008/131149. A process for preparing saxagliptin is also disclosed in WO 2005/106011 and WO 2005/115982. Saxagliptin can be formulated in a tablet as described in WO 2005/117841.

For details, e.g. on a process to manufacture, to formulate or to use this compound or a salt thereof, reference is thus made to these documents.

Alogliptin (SYR-322) having the structural formula E below is 2-({6-[(3R)-3-aminopiperidin-1-yl]-3-methyl-2,4-dioxo-3,4-dihydro-2H-pyrimidin-1-yl}methyl) benzonitrile

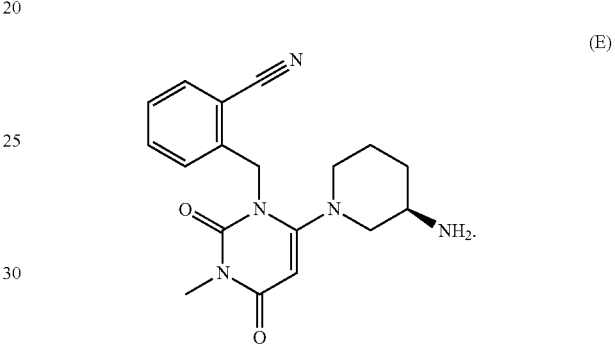

(E)

Alogliptin is specifically disclosed in US 2005/261271, EP 1586571 and in WO 2005/095381. In one embodiment, alogliptin is in the form of its benzoate salt, its hydrochloride salt or its tosylate salt each as disclosed in WO 2007/035629. A class of this embodiment refers to alogliptin benzoate. Polymorphs of alogliptin benzoate are disclosed in WO 2007/035372. A process for preparing alogliptin is disclosed in WO 2007/112368 and, specifically, in WO 2007/035629. Alogliptin (namely its benzoate salt) can be formulated in a tablet and administered as described in WO 2007/033266. A solid preparation of alogliptin/pioglitazone and its preparation and use is described in WO 2008/093882. A solid preparation of alogliptin/metformin and its preparation and use is described in WO 2009/011451. For details, e.g. on a process to manufacture, to formulate or to use this compound or a salt thereof, reference is thus made to these documents.

(2S)-1-{[2-(5-Methyl-2-phenyl-oxazol-4-yl)-ethyl amino]-acetyl}-pyrrolidine-2-carbonitrile or a pharmaceutically acceptable salt thereof, preferably the mesylate, or (2S)-1-{[1,1,-Dimethyl-3-(4-pyridin-3-yl-imidazol-1-yl)-propyl amino]-acetyl}-pyrrolidine-2-carbonitrile or a pharmaceutically acceptable salt thereof:

These compounds and methods for their preparation are disclosed in WO 03/037327. The mesylate salt of the former compound as well as crystalline polymorphs thereof are disclosed in WO 2006/100181. The fumarate salt of the latter compound as well as crystalline polymorphs thereof are disclosed in WO 2007/071576. These compounds can be formulated in a pharmaceutical composition as described in WO 2007/017423.

For details, e.g. on a process to manufacture, to formulate or to use these compounds or salts thereof, reference is thus made to these documents.

(S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one (also named carmegliptin) or a pharmaceutically acceptable salt thereof:

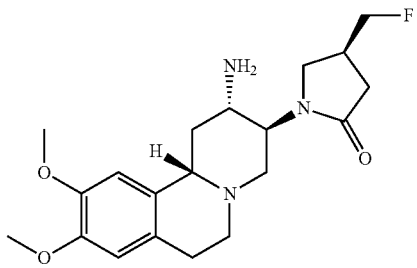 [SMILES: COc1cc2c(cc1OC)[C@@H]1C[C@H](N)[C@@H](N3C[C@@H](CF)CC3=O)CN1CC2]

This compound and methods for its preparation are disclosed in WO 2005/000848. A process for preparing this compound (specifically its dihydrochloride salt) is also disclosed in WO 2008/031749, WO 2008/031750 and WO 2008/055814. This compound can be formulated in a pharmaceutical composition as described in WO 2007/017423.

For details, e.g. on a process to manufacture, to formulate or to use this compound or a salt thereof, reference is thus made to these documents.

(3,3-Difluoropyrrolidin-1-yl)-((2S,4S)-4-(4-(pyrimidin-2-yl)piperazin-1-yl)pyrrolidin-2-yl)methanone (also named gosogliptin) or a pharmaceutically acceptable salt thereof:

This compound and methods for its preparation are disclosed in WO 2005/116014 and U.S. Pat. No. 7,291,618.

For details, e.g. on a process to manufacture, to formulate or to use this compound or a salt thereof, reference is thus made to these documents.

(1((3S,4S)-4-amino-1-(4-(3,3-difluoropyrrolidin-1-yl)-1,3,5-triazin-2-yl)pyrrolidin-3-yl)-5,5-difluoropiperidin-2-one or a pharmaceutically acceptable salt thereof:

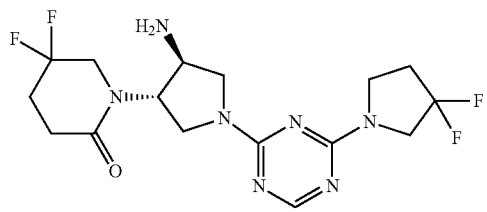 [SMILES: N[C@H]1CN(c2ncnc(N3CCC(F)(F)C3)n2)C[C@@H]1N1CC(F)(F)CCC1=O]

This compound and methods for its preparation are disclosed in WO 2007/148185 and US 20070299076. For details, e.g. on a process to manufacture, to formulate or to use this compound or a salt thereof, reference is thus made to these documents.

(2S,4S)-1-{2-[(3S,1R)-3-(1H-1,2,4-Triazol-1-ylmethyl)cyclopentylamino]-acetyl}-4-fluoropyrrolidine-2-carbonitrile (also named melogliptin) or a pharmaceutically acceptable salt thereof:

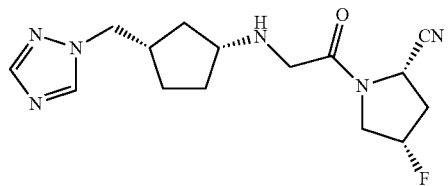 [SMILES: N#C[C@@H]1C[C@H](F)CN1C(=O)CN[C@@H]1CC[C@H](Cn2cncn2)C1]

This compound and methods for its preparation are disclosed in WO 2006/040625 and WO 2008/001195. Specifically claimed salts include the methanesulfonate and p-toluenesulfonate. For details, e.g. on a process to manufacture, to formulate or to use this compound or a salt thereof, reference is thus made to these documents.

(R)-2-[6-(3-Amino-piperidin-1-yl)-3-methyl-2,4-dioxo-3,4-dihydro-2H-pyrimidin-1-ylmethyl]-4-fluoro-benzonitrile or a pharmaceutically acceptable salt thereof:

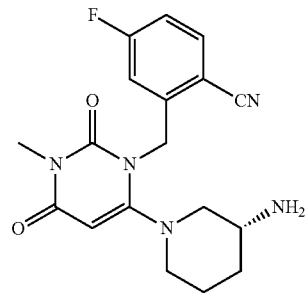 [SMILES: Cn1c(=O)cc(N2CCC[C@@H](N)C2)n(Cc2cc(F)ccc2C#N)c1=O]

This compound and methods for its preparation and use are disclosed in WO 2005/095381, US 2007060530, WO 2007/033350, WO 2007/035629, WO 2007/074884, WO 2007/112368, WO 2008/033851, WO 2008/114800 and WO 2008/114807. Specifically claimed salts include the succinate (WO 2008/067465), benzoate, benzenesulfonate, p-toluenesulfonate, (R)-mandelate and hydrochloride. For details, e.g. on a process to manufacture, to formulate or to use this compound or a salt thereof, reference is thus made to these documents.

5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide or a pharmaceutically acceptable salt thereof:

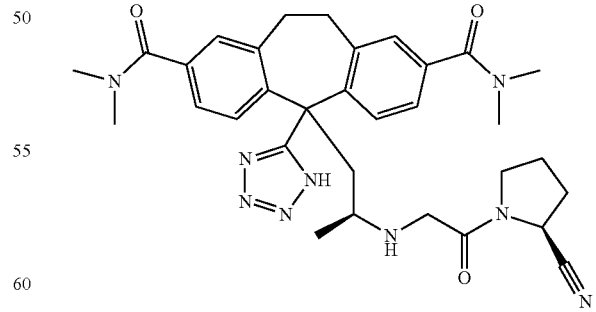

This compound and methods for its preparation are disclosed in WO 2006/116157 and US 2006/270701. For details, e.g. on a process to manufacture, to formulate or to use this compound or a salt thereof, reference is thus made to these documents.

3-{(2S,4S)-4-[4-(3-Methyl-1-phenyl-1H-pyrazol-5-yl)
piperazin-1-yl]pyrrolidin-2-ylcarbonyl}thiazolidine
(also named teneligliptin) or a pharmaceutically acceptable salt thereof:

This compound and methods for its preparation are disclosed in WO 02/14271. Specific salts are disclosed in WO 2006/088129 and WO 2006/118127 (including hydrochloride, hydrobromide, inter alia). Combination therapy using this compound is described in WO 2006/129785. For details, e.g. on a process to manufacture, to formulate or to use this compound or a salt thereof, reference is thus made to these documents.

[(2R)-1-{[(3R)-pyrrolidin-3-ylamino]acetyl}pyrrolidin-2-yl]boronic acid (also named dutogliptin) or a pharmaceutically acceptable salt thereof:

This compound and methods for its preparation are disclosed in WO 2005/047297, WO 2008/109681 and WO 2009/009751. Specific salts are disclosed in WO 2008/027273 (including citrate, tartrate). A formulation of this compound is described in WO 2008/144730. A formulation of dutogliptin (as its tartrate salt) with metformin is described in WO 2009/091663. For details, e.g. on a process to manufacture, to formulate or to use this compound or a salt thereof, reference is thus made to these documents.

(2S,4S)-1-[2-[(4-ethoxycarbonylbicyclo[2.2.2]oct-1-yl)
amino]acetyl]-4-fluoropyrrolidin-2-carbonitrile (also named bisegliptin) or a pharmaceutically acceptable salt thereof:

This compound and methods for its preparation are disclosed in WO 2005/075421, US 2008/146818 and WO 2008/114857. For details, e.g. on a process to manufacture, to formulate or to use this compound or a salt thereof, reference is thus made to these documents.

2-({6-[(3R)-3-amino-3-methylpiperidin-1-yl]-1,3-dimethyl-2,4-dioxo-1,2,3,4-tetrahydro-5H-pyrrolo[3,2-d]
pyrimidin-5-yl}methyl)-4-fluorobenzonitrile or a pharmaceutically acceptable salt thereof, or 6-[(3R)-3-
amino-piperidin-1-yl]-5-(2-chloro-5-fluoro-benzyl)-1,
3-dimethyl-1,5-dihydro-pyrrolo[3,2-d]pyrimidine-2,4-
dione or a pharmaceutically acceptable salt thereof:

These compounds and methods for their preparation are disclosed in WO 2009/084497 and WO 2006/068163, respectively. Combination therapy using the latter of these two compounds is described in WO 2009/128360. For details, e.g. on a process to manufacture, to formulate or to use these compounds or salts thereof, reference is thus made to these documents.

(S)-2-methylpyrazolo[1,5-a]perimidine-6-carboxylic acid
{2-[(2-cyanopyrrolidine-1-yl)-2-oxoethylamino]-2-
methylpropyl}amide (also named anagliptin) or a pharmaceutically acceptable salt:

This compound and methods for its preparation are disclosed in WO 2004/067509. Combination therapy using this compound is described in WO 2009/139362. For details, e.g. on a process to manufacture, to formulate or to use this compound or a salt thereof, reference is thus made to these documents.

Preferably the DPP-4 inhibitor of this invention is selected from the group (group G1) consisting of linagliptin, sitagliptin, vildagliptin, alogliptin, saxagliptin, teneligliptin, anagliptin, gemigliptin and dutogliptin, or a pharmaceutically acceptable salt of one of the hereinmentioned DPP-4 inhibitors, or a prodrug thereof.

A particularly preferred DPP-4 inhibitor within the present invention is linagliptin. The term "linagliptin" as employed herein refers to linagliptin or a pharmaceutically acceptable salt thereof, including hydrates and solvates thereof, and crystalline forms thereof, preferably linagliptin refers to 1-[(4-methyl-quinazolin-2-yl)methyl]-3-methyl-7-(2-butyn-1-yl)-8-(3-(R)-amino-piperidin-1-yl)-xanthine. Crystalline forms are described in WO 2007/128721. Methods for the manufacture of linagliptin are described in the patent applications WO 2004/018468 and WO 2006/048427 for example. Linagliptin is distinguished from structurally comparable DPP-4 inhibitors, as it combines exceptional potency and a long-lasting effect with favourable pharmacological properties, receptor selectivity and a favourable side-effect profile or bring about unexpected therapeutic advantages or improvements in mono- or dual or triple combination therapy.

For avoidance of any doubt, the disclosure of each of the foregoing and following documents cited above in connection with the specified DPP-4 inhibitors is specifically incorporated herein by reference in its entirety.

A long-acting insulin within the meaning of the present invention includes, without being limited to, any of those long-acting insulins mentioned hereinabove and hereinbelow, preferably subcutaneously active long-acting insulins.

Examples of long-acting insulins may include (group G2): insulin glargine; insulin detemir; insulin degludec; insulin lispro PEGylated with high molecular weight poly(ethylene glycol) derivatives as disclosed in WO 2009/152128; amidated insulin glargine in the form of $Gly^{A21}$, $Arg^{B31}$, $Arg^{B32}$-$NH_2$ human insulin; $Lys^{B29}(N^{\epsilon}$-lithocholyl-$\gamma$-Glu) des(B30) human insulin;

$N^{\epsilon B29}$-$\omega$-carboxypentadecanoyl-$\gamma$-amino-butanoyl des (B30) human insulin; amidated insulin analogs as disclosed in WO 2009/087082 (especially one selected from claim 14 therein), or amidated insulin analogs as disclosed in WO 2009/087081 (especially one selected from claim 16 therein).

Preferred examples of long-acting insulins of this invention are insulin glargine, insulin detemir and insulin degludec.

Unless otherwise noted, according to this invention it is to be understood that the definitions of the active agents (including the DPP-4 inhibitors and long-acting insulin analogues) mentioned hereinabove and hereinbelow may also contemplate their pharmaceutically acceptable salts, and prodrugs, hydrates, solvates and polymorphic forms thereof. Particularly the terms of the therapeutic agents given herein refer to the respective active drugs. With respect to salts, hydrates and polymorphic forms thereof, particular reference is made to those which are referred to herein.

In an embodiment the combinations, compositions, methods and uses according to this invention relate to combinations wherein the DPP-4 inhibitor and the long-acting insulins are preferably selected according to the entries in the Table 1:

TABLE 1

| DPP-4 Inhibitor | long-acting insulin |
| --- | --- |
| selected from embodiment A | selected from group G2 |
| selected from embodiment A | insulin glargine |
| selected from embodiment A | insulin detemir |
| selected from embodiment A | insulin degludec |
| selected from embodiment B | selected from group G2 |
| selected from embodiment B | insulin glargine |
| selected from embodiment B | insulin detemir |
| selected from embodiment B | insulin degludec |
| selected from group G1 | selected from group G2 |
| selected from group G1 | insulin glargine |
| selected from group G1 | insulin detemir |
| selected from group G1 | insulin degludec |
| selected from group G1 plus metformin | selected from group G2 |

TABLE 1-continued

| DPP-4 Inhibitor | long-acting insulin |
| --- | --- |
| selected from group G1 plus metformin | insulin glargine |
| selected from group G1 plus metformin | insulin detemir |
| selected from group G1 plus metformin | insulin degludec |
| selected from group G1 plus pioglitazone | selected from group G2 |
| selected from group G1 plus pioglitazone | insulin glargine |
| selected from group G1 plus pioglitazone | insulin detemir |
| selected from group G1 plus pioglitazone | insulin degludec |
| linagliptin | selected from group G2 |
| linagliptin | insulin glargine |
| linagliptin | insulin detemir |
| linagliptin | insulin degludec |
| linagliptin combined with metformin | selected from group G2 |
| linagliptin combined with metformin | insulin glargine |
| linagliptin combined with metformin | insulin detemir |
| linagliptin combined with metformin | insulin degludec |
| linagliptin combined with pioglitazone | selected from group G2 |
| linagliptin combined with pioglitazone | insulin glargine |
| linagliptin combined with pioglitazone | insulin detemir |
| linagliptin combined with pioglitazone | insulin degludec |

In a particular embodiment (embodiment E) the combinations, compositions, methods and uses according to this invention relate to combinations wherein the DPP-4 inhibitor is linagliptin. According to this particular embodiment (embodiment E) the long-acting insulin is preferably selected according to the entries E1 to E3 in the Table 2:

TABLE 2

| Embodiment | long-acting insulin |
| --- | --- |
| E1 | insulin glargine |
| E2 | insulin detemir |
| E3 | insulin degludec |

Within this invention it is to be understood that the combinations, compositions or combined uses according to this invention may envisage the simultaneous, sequential or separate administration of the active components or ingredients.

In this context, "combination" or "combined" within the meaning of this invention may include, without being limited, fixed and non-fixed (e.g. free) forms (including kits) and uses, such as e.g. the simultaneous, sequential or separate use of the components or ingredients.

The present invention also provides a kit-of-parts or combination therapeutic product comprising
a) a pharmaceutical composition comprising a DPP-4 inhibitor as defined herein, optionally together with one or more pharmaceutically acceptable carriers and/or diluents, and
b) a pharmaceutical composition comprising a long-acting insulin as defined herein.

The present invention also provides a kit comprising
a) a DPP-4 inhibitor as defined herein, and
b) a long-acting insulin as defined herein,
and, optionally, instructions directing use of the DPP-4 inhibitor and the long-acting insulin in combination (e.g. simultaneously, separately, sequentially or chronologically staggered), e.g. for a purpose of this invention, such as e.g. for the treatment of type 2 diabetes in a (human) patient.

The present invention also provides a pharmaceutical composition or fixed dose combination comprising
a) a DPP-4 inhibitor as defined herein, and
b) a long-acting insulin as defined herein, and, optionally, one or more pharmaceutically acceptable carriers and/or diluents.

The present invention also provides a transdermal or subcutaneous (injectable) pharmaceutical composition, delivery system or device for systemic use comprising
a) a DPP-4 inhibitor as defined herein, and, optionally,
b) a long-acting insulin as defined herein,
and, optionally, one or more pharmaceutically acceptable carriers and/or diluents.

The combined administration of this invention may take place by administering the active components or ingredients together, such as e.g. by administering them simultaneously in one single or in two separate formulations or dosage forms. Alternatively, the administration may take place by administering the active components or ingredients sequentially, such as e.g. successively in two separate formulations or dosage forms.

For the combination therapy of this invention the active components or ingredients may be administered separately (which implies that they are formulated separately) or formulated altogether (which implies that they are formulated in the same preparation or in the same dosage form). Hence, the administration of one element of the combination of the present invention may be prior to, concurrent to, or subsequent to the administration of the other element of the combination. In one embodiment, for the combination therapy according to this invention the DPP-4 inhibitor and the long-acting insulin are administered in different formulations or different dosage forms. In another embodiment, for the combination therapy according to this invention the DPP-4 inhibitor and the long-acting insulin are administered in the same formulation or in the same dosage form.

Unless otherwise noted, combination therapy may refer to first line, second line or third line therapy, or initial or add-on combination therapy or replacement therapy.

With respect to embodiment A, the methods of synthesis for the DPP-4 inhibitors according to embodiment A of this invention are known to the skilled person. Advantageously, the DPP-4 inhibitors according to embodiment A of this invention can be prepared using synthetic methods as described in the literature. Thus, for example, purine derivatives of formula (I) can be obtained as described in WO 2002/068420, WO 2004/018468, WO 2005/085246, WO 2006/029769 or WO 2006/048427, the disclosures of which are incorporated herein. Purine derivatives of formula (II) can be obtained as described, for example, in WO 2004/050658 or WO 2005/110999, the disclosures of which are incorporated herein. Purine derivatives of formula (III) and (IV) can be obtained as described, for example, in WO 2006/068163, WO 2007/071738 or WO 2008/017670, the disclosures of which are incorporated herein. The preparation of those DPP-4 inhibitors, which are specifically mentioned hereinabove, is disclosed in the publications mentioned in connection therewith. Polymorphous crystal modifications and formulations of particular DPP-4 inhibitors are disclosed in WO 2007/128721 and WO 2007/128724, respectively, the disclosures of which are incorporated herein in their entireties. Formulations of particular DPP-4 inhibitors with metformin or other combination partners are described in WO 2009/121945, the disclosure of which is incorporated herein in its entirety.

Typical dosage strengths of the dual fixed combination (tablet) of linagliptin/metformin IR (immediate release) are 2.5/500 mg, 2.5/850 mg and 2.5/1000 mg, which may be administered 1-3 times a day, particularly twice a day.

Typical dosage strengths of the dual fixed combination (tablet) of linagliptin/metformin XR (extended release) are 5/500 mg, 5/1000 mg and 5/1500 mg (each one tablet) or 2.5/500 mg, 2.5/750 mg and 2.5/1000 mg (each two tablets), which may be administered 1-2 times a day, particularly once a day, preferably to be taken in the evening with meal.

The present invention further provides a DPP-4 inhibitor as defined herein for use in (add-on or initial) combination therapy with metformin (e.g. in a total daily amount from 500 to 2000 mg metformin hydrochloride, such as e.g. 500 mg, 850 mg or 1000 mg once or twice daily).

With respect to embodiment B, the methods of synthesis for the DPP-4 inhibitors of embodiment B are described in the scientific literature and/or in published patent documents, particularly in those cited herein.

The elements of the combination of this invention may be administered by various ways, for example by oral, buccal, sublingual, enterical, parenteral (e.g., transdermal, intramuscular or subcutaneous), inhalative (e.g., liquid or powder inhalation, aerosol), pulmonary, intranasal (e.g. spray), intraperitoneal, vaginal, rectal, or topical routes of administration and may be formulated, alone or together, in suitable dosage unit formulations containing conventional non-toxic pharmaceutically acceptable carriers, adjuvants and vehicles appropriate for each route of administration.

In a preferred embodiment, the component DPP-4 inhibitor of the combination according to the invention is preferably administered orally. In another preferred embodiment, the component long-acting insulin of the combination is preferably administered by injection (preferably subcutaneously). In another embodiment, the component long-acting insulin of the combination is administered by a transdermal delivery system.

Suitable doses and dosage forms of the DPP-4 inhibitors may be determined by a person skilled in the art and may include those described herein or in the relevant references.

For pharmaceutical application in warm-blooded vertebrates, particularly humans, the compounds of this invention are usually used in dosages from 0.001 to 100 mg/kg body weight, preferably at 0.01-15 mg/kg or 0.1-15 mg/kg, in each case 1 to 4 times a day. For this purpose, the compounds, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The pharmaceutical compositions according to this invention comprising the DPP-4 inhibitors as defined herein are thus prepared by the skilled person using pharmaceutically acceptable formulation excipients as described in the art and appropriate for the desired route of administration. Examples of such excipients include, without being restricted to diluents, binders, carriers, fillers, lubricants, flow promoters, crystallisation retardants, disintegrants, solubilizers, colorants, pH regulators, surfactants and emulsifiers.

Oral preparations or dosage forms of the DPP-4 inhibitor of this invention may be prepared according to known techniques.

Examples of suitable diluents for compounds according to embodiment A include cellulose powder, calcium hydrogen phosphate, erythritol, low substituted hydroxypropyl cellulose, mannitol, pregelatinized starch or xylitol.

Examples of suitable lubricants for compounds according to embodiment A include talc, polyethyleneglycol, calcium behenate, calcium stearate, hydrogenated castor oil or magnesium stearate.

Examples of suitable binders for compounds according to embodiment A include copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, or low-substituted hydroxypropylcellulose (L-HPC).

Examples of suitable disintegrants for compounds according to embodiment A include corn starch or crospovidone.

Suitable methods of preparing pharmaceutical formulations of the DPP-4 inhibitors according to embodiment A of the invention are
  direct tabletting of the active substance in powder mixtures with suitable tabletting excipients;
  granulation with suitable excipients and subsequent mixing with suitable excipients and subsequent tabletting as well as film coating; or
  packing of powder mixtures or granules into capsules.
Suitable granulation methods are
  wet granulation in the intensive mixer followed by fluidised bed drying;
  one-pot granulation;
  fluidised bed granulation; or
  dry granulation (e.g. by roller compaction) with suitable excipients and subsequent tabletting or packing into capsules.

An exemplary composition (e.g. tablet core) of a DPP-4 inhibitor according to embodiment A of the invention comprises the first diluent mannitol, pregelatinized starch as a second diluent with additional binder properties, the binder copovidone, the disintegrant corn starch, and magnesium stearate as lubricant; wherein copovidone and/or corn starch may be optional.

A tablet of a DPP-4 inhibitor according to embodiment A of the invention may be film coated, preferably the film coat comprises hydroxypropylmethylcellulose (HPMC), polyethylene glycol (PEG), talc, titanium dioxide and iron oxide (e.g. red and/or yellow).

In a further embodiment, the component DPP-4 inhibitor of the combination according to the invention is administered by injection (preferably subcutaneously). In another embodiment, the component long-acting insulin of the combination is preferably administered by injection (preferably subcutaneously) as well. In another embodiment, the component long-acting insulin of the combination is administered by a transdermal delivery system.

Injectable formulations of the long-acting insulin and/or the DPP-4 inhibitor of this invention (particularly for subcutaneous use) may be prepared according to known formulation techniques, e.g. using suitable liquid carriers, which usually comprise sterile water, and, optionally, further additives such as e.g. preservatives, pH adjusting agents, buffering agents, isotoning agents, solubility aids and/or tensides or the like, to obtain injectable solutions or suspensions. In addition, injectable formulations may comprise further additives, for example salts, solubility modifying agents or precipitating agents which retard release of the drug(s). In further addition, injectable insulin formulations may comprise insulin stabilizing agents, such as zinc compounds.

In a further embodiment, the component DPP-4 inhibitor of the combination according to the invention is administered by a transdermal delivery system. In another embodiment, the component long-acting insulin of the combination is administered by a transdermal delivery system as well. In another embodiment, the component long-acting insulin of the combination is preferably administered by injection (preferably subcutaneously). In another embodiment, the component long-acting insulin of the combination is administered by (subcutaneous implanted) insulin pellets.

Transdermal formulations (e.g. for transdermal patches or gels) of the long-acting insulin and/or the DPP-4 inhibitor of this invention may be prepared according to known formulation techniques, e.g. using suitable carriers and, optionally, further additives. To facilitate transdermal passage, different methodologies and systems may be used, such as e.g. techniques involving formation of microchannels or micropores in the skin, such as e.g. iontophoresis (based on low-level electrical current), sonophoresis (based on low-frequency ultrasound) or microneedling, or the use of drug-carrier agents (e.g. elastic or lipid vesicles such as transfersomes) or permeation enhancers.

For further details on dosage forms, formulations and administration of DPP-4 inhibitors of this invention and/or long-acting insulin of this invention, reference is made to scientific literature and/or published patent documents, particularly to those cited herein.

The pharmaceutical compositions (or formulations) may be packaged in a variety of ways. Generally, an article for distribution includes one or more containers that contain the one or more pharmaceutical compositions in an appropriate form. Tablets are typically packed in an appropriate primary package for easy handling, distribution and storage and for assurance of proper stability of the composition at prolonged contact with the environment during storage. Primary containers for tablets may be bottles or blister packs.

A suitable bottle, e.g. for a pharmaceutical composition or combination (tablet) comprising a DPP-4 inhibitor according to embodiment A of the invention, may be made from glass or polymer (preferably polypropylene (PP) or high density polyethylene (HD-PE)) and sealed with a screw cap. The screw cap may be provided with a child resistant safety closure (e.g. press-and-twist closure) for preventing or hampering access to the contents by children. If required (e.g. in regions with high humidity), by the additional use of a desiccant (such as e.g. bentonite clay, molecular sieves, or, preferably, silica gel) the shelf life of the packaged composition can be prolonged.

A suitable blister pack, e.g. for a pharmaceutical composition or combination (tablet) comprising a DPP-4 inhibitor according to embodiment A of the invention, comprises or is formed of a top foil (which is breachable by the tablets) and a bottom part (which contains pockets for the tablets). The top foil may contain a metallic foil, particularly aluminium or aluminium alloy foil (e.g. having a thickness of 20 μm to 45 μm, preferably 20 μm to 25 μm) that is coated with a heat-sealing polymer layer on its inner side (sealing side). The bottom part may contain a multi-layer polymer foil (such as e.g. poly(vinyl chloride) (PVC) coated with poly(vinylidene chloride) (PVDC); or a PVC foil laminated with poly(chlorotrifluoroethylene) (PCTFE)) or a multi-layer polymer-metal-polymer foil (such as e.g. a cold-formable laminated PVC/aluminium/polyamide composition).

To ensure a long storage period especially under hot and wet climate conditions an additional overwrap or pouch made of a multi-layer polymer-metal-polymer foil (e.g. a laminated polyethylene/aluminium/polyester composition) may be used for the blister packs. Supplementary desiccant (such as e.g. bentonite clay, molecular sieves, or, preferably, silica gel) in this pouch package may prolong the shelf life even more under such harsh conditions.

Solutions for injection may be available in typical suitable presentation forms such as vials, cartridges or prefilled (disposable) pens, which may be further packaged.

The article may further comprise a label or package insert, which refer to instructions customarily included in commercial packages of therapeutic products, that may contain information about the indications, usage, dosage, administration, contraindications and/or warnings concerning the use of such therapeutic products. In one embodiment, the label or package inserts indicates that the composition can be used for any of the purposes described herein.

With respect to the first embodiment (embodiment A), the dosage typically required of the DPP-4 inhibitors mentioned herein in embodiment A when administered intravenously is 0.1 mg to 10 mg, preferably 0.25 mg to 5 mg, and when administered orally is 0.5 mg to 100 mg, preferably 2.5 mg to 50 mg or 0.5 mg to 10 mg, more preferably 2.5 mg to 10 mg or 1 mg to 5 mg, in each case 1 to 4 times a day. Thus, e.g. the dosage of 1-[(4-methyl-quinazolin-2-yl)methyl]-3-methyl-7-(2-butyn-1-yl)-8-(3-(R)-amino-piperidin-1-yl)-xanthine when administered orally is 0.5 mg to 10 mg per patient per day, preferably 2.5 mg to 10 mg or 1 mg to 5 mg per patient per day.

A dosage form prepared with a pharmaceutical composition comprising a DPP-4 inhibitor mentioned herein in embodiment A contain the active ingredient in a dosage range of 0.1-100 mg. Thus, e.g. particular oral dosage strengths of 1-[(4-methyl-quinazolin-2-yl)methyl]-3-methyl-7-(2-butyn-1-yl)-8-(3-(R)-amino-piperidin-1-yl)-xanthine are 0.5 mg, 1 mg, 2.5 mg, 5 mg and 10 mg.

With respect to the second embodiment (embodiment B), the doses of DPP-4 inhibitors mentioned herein in embodiment B to be administered to mammals, for example human beings, of, for example, approximately 70 kg body weight, may be generally from about 0.5 mg to about 350 mg, for example from about 10 mg to about 250 mg, preferably 20-200 mg, more preferably 20-100 mg, of the active moiety per person per day, or from about 0.5 mg to about 20 mg, preferably 2.5-10 mg, per person per day, divided preferably into 1 to 4 single doses which may, for example, be of the same size. Single oral dosage strengths comprise, for example, 10, 25, 40, 50, 75, 100, 150 and 200 mg of the DPP-4 inhibitor active moiety.

An oral dosage strength of the DPP-4 inhibitor sitagliptin is usually between 25 and 200 mg of the active moiety. A recommended dose of sitagliptin is 100 mg calculated for the active moiety (free base anhydrate) once daily. Unit dosage strengths of sitagliptin free base anhydrate (active moiety) are 25, 50, 75, 100, 150 and 200 mg. Particular unit dosage strengths of sitagliptin (e.g. per tablet) are 25, 50 and 100 mg. An equivalent amount of sitagliptin phosphate monohydrate to the sitagliptin free base anhydrate is used in the pharmaceutical compositions, namely, 32.13, 64.25, 96.38, 128.5, 192.75, and 257 mg, respectively. Adjusted dosages of 25 and 50 mg sitagliptin are used for patients with renal failure. Typical dosage strengths of the dual combination of sitagliptin/metformin are 50/500 mg and 50/1000 mg.

An oral dosage range of the DPP-4 inhibitor vildagliptin is usually between 10 and 150 mg daily, in particular between 25 and 150 mg, 25 and 100 mg or 25 and 50 mg or 50 and 100 mg daily. Particular examples of daily oral dosage are 25, 30, 35, 45, 50, 55, 60, 80, 100 or 150 mg. In a more particular aspect, the daily administration of vildagliptin may be between 25 and 150 mg or between 50 and 100 mg. In another more particular aspect, the daily administration of vildagliptin may be 50 or 100 mg. The application of the active ingredient may occur up to three times a day, preferably one or two times a day. Particular dosage strengths are 50 mg or 100 mg vildagliptin. Typical dosage strengths of the dual combination of vildagliptin/metformin are 50/850 mg and 50/1000 mg.

Alogliptin may be administered to a patient at an oral daily dose of between 5 mg/day and 250 mg/day, optionally between 10 mg and 200 mg, optionally between 10 mg and 150 mg, and optionally between 10 mg and 100 mg of alogliptin (in each instance based on the molecular weight of the free base form of alogliptin). Thus, specific oral dosage amounts that may be used include, but are not limited to 10 mg, 12.5 mg, 20 mg, 25 mg, 50 mg, 75 mg and 100 mg of alogliptin per day. Alogliptin may be administered in its free base form or as a pharmaceutically acceptable salt.

Saxagliptin may be administered to a patient at an oral daily dose of between 2.5 mg/day and 100 mg/day, optionally between 2.5 mg and 50 mg. Specific oral dosage amounts that may be used include, but are not limited to 2.5 mg, 5 mg, 10 mg, 15 mg, 20 mg, 30 mg, 40 mg, 50 mg and 100 mg of saxagliptin per day. Typical dosage strengths of the dual combination of saxagliptin/metformin are 2.5/500 mg and 2.5/1000 mg.

A special embodiment of the DPP-4 inhibitors of this invention refers to those orally administered DPP-4 inhibitors which are therapeutically efficacious at low dose levels, e.g. at oral dose levels <100 mg or <70 mg per patient per day, preferably <50 mg, more preferably <30 mg or <20 mg, even more preferably from 1 mg to 10 mg, particularly from 1 mg to 5 mg (more particularly 5 mg), per patient per day (if required, divided into 1 to 4 single doses, particularly 1 or 2 single doses, which may be of the same size, preferentially, administered orally once- or twice daily (more preferentially once-daily), advantageously, administered at any time of day, with or without food. Thus, for example, the daily oral amount 5 mg BI 1356 can be given in an once daily dosing regimen (i.e. 5 mg BI 1356 once daily) or in a twice daily dosing regimen (i.e. 2.5 mg BI 1356 twice daily), at any time of day, with or without food.

The long-acting insulin is typically administered by subcutaneous injection, e.g. ranging from twice daily, once daily to once weekly injection. Suitable doses and dosage forms of the long-acting insulin may be determined by a person skilled in the art. Blood glucose monitoring is essential in all patients receiving insulin therapy.

For example, insulin glargine (Lantus) is administered subcutaneously once a day. Lantus may be administered at any time during the day, but at the same time every day. The dose of Lantus is individualized based on clinical response. The recommended starting dose of Lantus in patients with type 2 diabetes who are not currently treated with insulin is 10 units (or 0.2 Units/kg) once daily, which should subsequently be adjusted to the patient's needs.

Insulin detemir (Levemir) is administered subcutaneously once or twice a day. For patients treated with Levemir once daily, the dose is preferably administered with the evening meal or at bedtime. For patients who require twice-daily dosing, the evening dose can be administered either with evening meal, at bedtime, or 12 hours after the morning dose. The dose of Levemir is individualized based on clinical response. For insulin-naive patients with type 2 diabetes who are inadequately controlled on oral antidiabetic drugs, Levemir should be started at a dose of 0.1 to 0.2 Units/kg once-daily in the evening or 10 units once- or twice-daily, and the dose adjusted to achieve glycemic targets.

The dosage of the active ingredients in the combinations and compositions in accordance with the present invention may be varied, although the amount of the active ingredients shall be such that a suitable dosage form is obtained. Hence, the selected dosage and the selected dosage form shall depend on the desired therapeutic effect, the route of administration and the duration of the treatment. Suitable dosage ranges for the combination are from the maximal tolerated dose for the single agent to lower doses, e.g. to one tenth of the maximal tolerated dose.

A particularly preferred DPP-4 inhibitor to be emphasized within the meaning of this invention is 1-[(4-methyl-quinazolin-2-yl)-methyl]-3-methyl-7-(2-butyn-1-yl)-8-(3-(R)-amino-piperidin-1-yl)-xanthine (also known as BI 1356 or linagliptin). BI 1356 exhibits high potency, 24 h duration of action, and a wide therapeutic window. In patients with type 2 diabetes receiving multiple oral doses of 1, 2.5, 5 or 10 mg of BI 1356 once daily for 12 days, BI 1356 shows favourable pharmacodynamic and pharmacokinetic profile (see e.g. Table 3 below) with rapid attainment of steady state (e.g. reaching steady state plasma levels (>90% of the pre-dose plasma concentration on Day 13) between second and fifth day of treatment in all dose groups), little accumulation (e.g. with a mean accumulation ratio $R_{A,AUC}$≤1.4 with doses above 1 mg) and preserving a long-lasting effect on DPP-4 inhibition (e.g. with almost complete (>90%) DPP-4 inhibition at the 5 mg and 10 mg dose levels, i.e. 92.3 and 97.3% inhibition at steady state, respectively, and >80% inhibition over a 24 h interval after drug intake), as well as significant decrease in 2 h postprandial blood glucose excursions by ≥80% (already on Day 1) in doses ≥2.5 mg, and with the cumulative amount of unchanged parent compound excreted in urine on Day 1 being below 1% of the administered dose and increasing to not more than about 3-6% on Day 12 (renal clearance $CL_{R,ss}$ is from about 14 to about 70 mL/min for the administered oral doses, e.g. for the 5 mg dose renal clearance is about 70 ml/min). In people with type 2 diabetes BI 1356 shows a placebo-like safety and tolerability. With low doses of about ≥5 mg, BI 1356 acts as a true once-daily oral drug with a full 24 h duration of DPP-4 inhibition. At therapeutic oral dose levels, BI 1356 is mainly excreted via the liver and only to a minor extent (about <7% of the administered oral dose) via the kidney. BI 1356 is primarily excreted unchanged via the bile. The fraction of BI 1356 eliminated via the kidneys increases only very slightly over time and with increasing dose, so that there will likely be no need to modify the dose of BI 1356 based on the patients' renal function. The non-renal elimination of BI 1356 in combination with its low accumulation potential and broad safety margin may be of significant benefit in a patient population that has a high prevalence of renal insufficiency and diabetic nephropathy.

TABLE 3

Geometric mean (gMean) and geometric coefficient of variation (gCV) of pharmacokinetic parameters of BI 1356 at steady state (Day 12)

| Parameter | 1 mg gMean (gCV) | 2.5 mg gMean (gCV) | 5 mg gMean (gCV) | 10 mg gMean (gCV) |
|---|---|---|---|---|
| $AUC_{0-24}$ [nmol · h/L] | 40.2 (39.7) | 85.3 (22.7) | 118 (16.0) | 161 (15.7) |
| $AUC_{\tau,ss}$ [nmol · h/L] | 81.7 (28.3) | 117 (16.3) | 158 (10.1) | 190 (17.4) |
| $C_{max}$ [nmol/L] | 3.13 (43.2) | 5.25 (24.5) | 8.32 (42.4) | 9.69 (29.8) |

TABLE 3-continued

Geometric mean (gMean) and geometric coefficient of variation (gCV) of pharmacokinetic parameters of BI 1356 at steady state (Day 12)

| Parameter | 1 mg gMean (gCV) | 2.5 mg gMean (gCV) | 5 mg gMean (gCV) | 10 mg gMean (gCV) |
|---|---|---|---|---|
| $C_{max,ss}$ [nmol/L] | 4.53 (29.0) | 6.58 (23.0) | 11.1 (21.7) | 13.6 (29.6) |
| $t_{max}$* [h] | 1.50 [1.00-3.00] | 2.00 [1.00-3.00] | 1.75 [0.92-6.02] | 2.00 [1.50-6.00] |
| $t_{max,ss}$* [h] | 1.48 [1.00-3.00] | 1.42 [1.00-3.00] | 1.53 [1.00-3.00] | 1.34 [0.50-3.00] |
| $T_{1/2,ss}$ [h] | 121 (21.3) | 113 (10.2) | 131 (17.4) | 130 (11.7) |
| Accumulation $t_{1/2}$ [h] | 23.9 (44.0) | 12.5 (18.2) | 11.4 (37.4) | 8.59 (81.2) |
| $R_{A,Cmax}$ | 1.44 (25.6) | 1.25 (10.6) | 1.33 (30.0) | 1.40 (47.7) |
| $R_{A,AUC}$ | 2.03 (30.7) | 1.37 (8.2) | 1.33 (15.0) | 1.18 (23.4) |
| $fe_{0-24}$ [%] | NC | 0.139 (51.2) | 0.453 (125) | 0.919 (115) |
| $fe_{\tau,ss}$ [%] | 3.34 (38.3) | 3.06 (45.1) | 6.27 (42.2) | 3.22 (34.2) |
| $CL_{R,ss}$ [mL/min] | 14.0 (24.2) | 23.1 (39.3) | 70 (35.0) | 59.5 (22.5) |

*median and range [min-max]
NC not calculated as most values below lower limit of quantification As different metabolic functional disorders often occur simultaneously, it is quite often indicated to combine a number of different active principles with one another. Thus, depending on the functional disorders diagnosed, improved treatment outcomes may be obtained if a DPP-4 inhibitor is combined with active substances customary for the respective disorders, such as e.g. one or more active substances selected from among the other antidiabetic substances, especially active substances that lower the blood sugar level or the lipid level in the blood, raise the HDL level in the blood, lower blood pressure or are indicated in the treatment of atherosclerosis or obesity.

The DPP-4 inhibitors mentioned above—besides their use in mono-therapy—may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; mitiglinide; thiazolidinediones such as rosiglitazone and pioglitazone; PPAR gamma modulators such as metaglidases; PPAR-gamma agonists such as e.g. rivoglitazone, mitoglitazone, INT-131 and balaglitazone; PPAR-gamma antagonists; PPAR-gamma/alpha modulators such as tesaglitazar, muraglitazar, aleglitazar, indeglitazar and KRP297; PPAR-gamma/alpha/delta modulators such as e.g. lobeglitazone; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as SMT3-receptor-agonists and GPR119, such as the GPR119 agonists 5-ethyl-2-{4-[4-(4-tetrazol-1-yl-phenoxymethyl)-thiazol-2-yl]-piperidin-1-yl}-pyrimidine or 5-[1-(3-isopropyl-[1,2,4]oxadiazol-5-yl)-piperidin-4-ylmethoxy]-2-(4-methanesulfonyl-phenyl)-pyridine; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin degludec, insulin tregopil, insulin zinc suspension and insulin glargin; Gastric inhibitory Peptide (GIP); amylin and amylin analogues (e.g. pramlintide or davalintide); GLP-1 and GLP-1 analogues such as Exendin-4, e.g. exenatide, exenatide LAR, liraglutide, taspoglutide, lixisenatide (AVE-0010), LY-2428757 (a PEGylated version of GLP-1), dulaglutide (LY-2189265), semaglutide or albiglutide; SGLT2-inhibitors such as e.g. dapagliflozin, sergliflozin (KGT-1251), atigliflozin, canagliflozin, ipragliflozin, luseogliflozin or tofogliflozin; inhibitors of protein tyrosine-phosphatase (e.g. trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093, 330, WO 2004/005281, and WO 2006/041976) or of serine/threonine kinases; glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta δ agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors; KV 1.3 channel inhibitors; GPR40 modulators such as e.g. [(3S)-6-(12',6'-dimethyl-4'-[3-(methylsulfonyl)propoxylbiphenyl-3-yl]methoxy)-2,3-dihydro-1-benzofuran-3-yl]acetic acid; SCD-1 inhibitors; CCR-2 antagonists; dopamine receptor agonists (bromocriptine mesylate [Cycloset]); 4-(3-(2,6-dimethylbenzyloxy)phenyl)-4-oxobutanoic acid; sirtuin stimulants; and other DPP IV inhibitors.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

For children 10 to 16 years of age, the recommended starting dose of metformin is 500 mg given once daily. If this dose fails to produce adequate results, the dose may be increased to 500 mg twice daily. Further increases may be made in increments of 500 mg weekly to a maximum daily dose of 2000 mg, given in divided doses (e.g. 2 or 3 divided doses). Metformin may be administered with food to decrease nausea.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (or up to 40 mg divided twice) a day (typical dosage strengths are 5 and 10 mg), or extended-release glibenclamide in doses from 5 to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

A dual combination of glibenclamide/metformin is usually given in doses from 1.25/250 once daily to 10/1000 mg twice daily. (typical dosage strengths are 1.25/250, 2.5/500 and 5/500 mg).

A dual combination of glipizide/metformin is usually given in doses from 2.5/250 to 10/1000 mg twice daily (typical dosage strengths are 2.5/250, 2.5/500 and 5/500 mg).

A dual combination of glimepiride/metformin is usually given in doses from 1/250 to 4/1000 mg twice daily.

A dual combination of rosiglitazone/glimepiride is usually given in doses from 4/1 once or twice daily to 4/2 mg twice daily (typical dosage strengths are 4/1, 4/2, 4/4, 8/2 and 8/4 mg).

A dual combination of pioglitazone/glimepiride is usually given in doses from 30/2 to 30/4 mg once daily (typical dosage strengths are 30/4 and 45/4 mg).

A dual combination of rosiglitazone/metformin is usually given in doses from 1/500 to 4/1000 mg twice daily (typical dosage strengths are 1/500, 2/500, 4/500, 2/1000 and 4/1000 mg).

A dual combination of pioglitazone/metformin is usually given in doses from 15/500 once or twice daily to 15/850 mg thrice daily (typical dosage strengths are 15/500 and 15/850 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

Acarbose is usually given in doses from 25 to 100 mg with meals. Miglitol is usually given in doses from 25 to 100 mg with meals.

Examples of combination partners that lower the lipid level in the blood are HMG-CoA-reductase inhibitors such as simvastatin, atorvastatin, lovastatin, fluvastatin, pravastatin, pitavastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists such as e.g. {4-[(R)-2-ethoxy-3-(4-trifluoromethyl-phenoxy)-propylsulfanyl]-2-methyl-phenoxy}-acetic acid; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 (dalcetrapib) or compound 12 from WO 2007/005572 (anacetrapib); LDL receptor modulators; MTP inhibitors (e.g. lomitapide); and ApoB100 antisense RNA.

A dosage of atorvastatin is usually from 1 mg to 40 mg or 10 mg to 80 mg once a day.

Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan, azilsartan and eprosartan.

A dosage of telmisartan is usually from 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apolipoprotein A-I.

Examples of combination partners for the treatment of obesity are sibutramine; tetrahydrolipstatin (orlistat); alizyme (cetilistat); dexfenfluramine; axokine; cannabinoid receptor 1 antagonists such as the CB1 antagonist rimonobant; MCH-1 receptor antagonists; MC4 receptor agonists; NPY5 as well as NPY2 antagonists (e.g. velneperit); beta3-AR agonists such as SB-418790 and AD-9677; 5HT2c receptor agonists such as APD 356 (lorcaserin); myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine; as well as the dual combinations bupropion/naltrexone, bupropion/zonisamide, topiramate/phentermine and pramlintide/meterleptin.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

Linagliptin s.c. Dosing and its DPP-4 Inhibition in Plasma

Linagliptin subcutaneous (s.c.) dosing and DPP-4 inhibition in plasma can be comparable in efficacy and duration of action to oral dosing, which may make it suitable for use in fixed combination with s.c. insulin:

Male ZDF rats (n=5) have been treated with different concentrations of BI 1356 in a subcutaneous (s.c.) administration regimen (0.001 mg/kg, 0.01 mg/kg, 0.1 mg/kg and 1 mg/kg in 0.5 ml/kg NaCl solution) in comparison to 3 mg/kg p.o. (in 0.5% Natrosol, 5 ml/kg volume of application).

DPP-4 activity in EDTA plasma was detected 1, 3, 5, 7, 24, 31, 48, 72 h following drug administration (blood was taken by venous puncture under isofluran anesthesia from the vena sublingualis).

Doses of BI 1356 from 0.01 mg/kg (s.c. administered) on demonstrated significant inhibition of DPP-4 activity compared to control. The dose of 0.1 mg/kg and 1 mg/kg (s.c. administration) of BI 1356 had a persistent DPP-4 inhibition of more than 64% over 7 h. The 1 mg/kg s.c. dose was comparable in efficacy and duration of action to the 3 mg/kg oral dose. The results are shown in FIG. 1.

Effect of Linagliptin on Body Weight Total Body Fat, Liver Fat and Intramyocellular Fat In a further study the efficacy of chronic treatment with linagliptin on body weight, total body fat, intra-myocellular fat, and hepatic fat in a non-diabetic model of diet induced obesity (DIO) in comparison to the appetite suppressant sibutramine is investigated:

Rats are fed a high-fat diet for 3 months and received either vehicle, linagliptin (10 mg/kg), or sibutramine (5 mg/kg) for 6 additional weeks, while continuing the high-fat diet. Magnetic resonance spectroscopy (MRS) analysis of total body fat, muscle fat, and liver fat is performed before treatment and at the end of the study.

Sibutramine causes a significant reduction of body weight (−12%) versus control, whereas linagliptin has no significant effect (−3%). Total body fat is also significantly reduced by sibutramine (−12%), whereas linagliptin-treated animals show no significant reduction (−5%). However, linagliptin and sibutramine result both in a potent reduction of intramyocellular fat (−24% and −34%, respectively). In addition, treatment with linagliptin results in a profound decrease of hepatic fat (−39%), whereas the effect of sibutramine (−30%) does not reach significance (see Table 4). Thus, linagliptin is weight neutral but improves intra-myocellular and hepatic lipid accumulation.

attempt to evaluate the effect of linagliptin on pancreatic inflammation and beta-cell mass it is examined the progression of diabetes in the non-obese-diabetic (NOD) mice over a 60 day experimental period coupled with terminal stereological assessment of cellular pancreatic changes.

Sixty female NOD mice (10 weeks of age) are included in the study and fed a normal chow diet or a diet containing linagliptin (0.083 g linagliptin/kg chow; corresponding to 3-10 mg/kg, p.o) throughout the study period. Bi-weekly plasma samples are obtained to determine onset of diabetes (BG>11 mmol/l). At termination, the pancreata are removed and a terminal blood sample is obtained for assessment of active GLP-1 levels.

At the end of the study period the incidence of diabetes is significantly decreased in linagliptin-treated mice (9 out of 30 mice) compared with the control group (18 of 30 mice, p=0.021). The subsequent stereological assessment of beta-cell mass (identified by insulin immunoreactivity) demonstrates a significantly larger beta cell mass (vehicle 0.18±0.03 mg; linagliptin 0.48±0.09 mg, p<0.01) and total islet mass (vehicle 0.40±0.04 mg; linagliptin 0.70±0.09 mg, p<0.01) in linagliptin treated mice. There is a tendency for linagliptin to reduce peri-islet infiltrating lymphocytes (1.06±0.15; linagliptin 0.79±0.12 mg, p=0.17). As expected active plasma GLP-1 are higher at termination in linagliptin treated mice. In summary, the data demonstrate that linagliptin is able to delay the onset of diabetes in a type-1 diabetic model (NOD mouse). The pronounced beta-cell sparing effects which can be observed in this animal model indicate that such DPP-4 inhibition not only protects beta-cells by increasing active GLP-1 levels, but may also exerts direct or indirect anti-inflammatory actions.

The invention claimed is:

1. A method for treating type 2 diabetes in a patient in need thereof, the method comprising subcutaneously or transdermally administering linagliptin and basal insulin, and, optionally, administering a further therapeutic agent selected from metformin and pioglitazone, wherein the administration of linagliptin and basal insulin is carried out separately, sequentially, or simultaneously.

TABLE 4

Effect of linagliptin on body weight total body fat, liver fat and intramyocellular fat

| | Body weight | | Total body fat | | Liver fat | | intra-myocellular fat | |
|---|---|---|---|---|---|---|---|---|
| | % contr. | % baseli. | % contr. | % baseli. | % contr. | % baseli. | % contr. | % baseli. |
| Control | — | +15% | — | +11% | — | +27% | — | +23% |
| | | p = 0.016 | | p = 0.001 | | p = 0.09 | | p = 0.49 |
| Linagliptin | −3% | +12% | −5% | +5% | −39% | −30% | −36% | −24% |
| | p = 0.56 | p = 0.001 | p = 0.27 | p = 0.06 | p = 0.022 | p = 0.05 | p = 0.14 | p = 0.039 |
| Sibutramine | −12% | +1% | −12% | −0.4% | −30% | −29% | −55% | −34% |
| | p = 0.018 | p = 0.64 | p = 0.008 | p = 0.86 | p = 0.13 | p = 0.12 | p = 0.037 | p = 0.007 |

In conclusion, linagliptin treatment provokes a potent reduction of intramyocellular lipids and hepatic fat, which are both independent of weight loss. The effects of sibutramine on muscular and hepatic fat are attributed mainly to the known weight reduction induced by this compound.

Delaying Onset of Diabetes and Preserving Beta-Cell Function in Non-Obese Type-1 Diabetes:

Though reduced pancreatic T-cell migration and altered cytokine production is considered important players for the onset of insulinitis the exact mechanism and effects on the pancreatic cell pool is still incompletely understood. In an 2. The method of claim 1 wherein the long-acting basal insulin is insulin detemir, insulin glargine, or insulin degludec.

3. A method of treating type 2 diabetes, the method comprising subcutaneously or transdermally administering linagliptin once daily, every other day, thrice weekly, twice weekly, or once weekly.

4. The method according to claim 1, wherein the linagliptin is administered subcutaneously.

5. The method according to claim 1, wherein the linagliptin is administered transdermally.

6. The method according to claim 1, wherein the basal insulin is administered subcutaneously.

7. The method according to claim 1, wherein the basal insulin is administered transdermally.

8. The method according to claim 1, wherein both the basal insulin and linagliptin are administered subcutaneously.

* * * * *